(12) United States Patent
Dehury et al.

(10) Patent No.: US 9,206,163 B2
(45) Date of Patent: Dec. 8, 2015

(54) PROCESS FOR THE PREPARATION OF SUNITINIB AND ITS ACID ADDITION SALTS THEREOF

(71) Applicant: Laurus Labs Private Limited, Hyderabad (IN)

(72) Inventors: Sanjay Kumar Dehury, Hyderabad (IN); Venkata Lakshmi Narasimha Dammalapati, Hyderabad (IN); Venkata Sunil Kumar Indukuri, Hyderabad (IN); Seeta Ramanjaneyulu Gorantla, Hyderabad (IN)

(73) Assignee: Laurus Labs Private Ltd. (IN)

( * ) Notice: Subject to any disclaimer, the term of this patent is extended or adjusted under 35 U.S.C. 154(b) by 0 days.

(21) Appl. No.: 14/381,546

(22) PCT Filed: Mar. 22, 2013

(86) PCT No.: PCT/IB2013/000459
§ 371 (c)(1),
(2) Date: Aug. 27, 2014

(87) PCT Pub. No.: WO2013/140232
PCT Pub. Date: Sep. 26, 2013

(65) Prior Publication Data
US 2015/0025252 A1 Jan. 22, 2015

(30) Foreign Application Priority Data
Mar. 23, 2012 (IN) .............................. 1083/CHE/2012

(51) Int. Cl.
| | | |
|---|---|---|
| C07D 403/06 | (2006.01) |
| A61K 31/404 | (2006.01) |
| C07C 53/134 | (2006.01) |
| C07C 55/07 | (2006.01) |
| C07C 55/10 | (2006.01) |
| C07C 59/245 | (2006.01) |

(52) U.S. Cl.
CPC ............ *C07D 403/06* (2013.01); *A61K 31/404* (2013.01); *C07C 53/134* (2013.01); *C07C 55/07* (2013.01); *C07C 55/10* (2013.01); *C07C 59/245* (2013.01)

(58) Field of Classification Search
CPC ....................................................... C07D 403/06
USPC ................................................................ 548/468
See application file for complete search history.

(56) References Cited

U.S. PATENT DOCUMENTS

| | | | | |
|---|---|---|---|---|
| 6,797,725 | B2 * | 9/2004 | Sun ....................... | C07D 403/06 514/399 |
| 8,329,740 | B2 * | 12/2012 | Reddy .................. | C07D 403/06 514/414 |
| 8,703,967 | B2 * | 4/2014 | Selic ..................... | C07D 403/06 548/468 |
| 8,916,716 | B2 * | 12/2014 | Sanwal ................ | C07D 403/06 548/468 |
| 2005/0059824 | A1 | 3/2005 | Vaidyanathan et al. | |
| 2006/0009510 | A1 | 1/2006 | Havens et al. | |
| 2011/0257237 | A1 * | 10/2011 | Gaitonde ............. | C07D 403/06 514/414 |
| 2012/0271056 | A1 * | 10/2012 | Sanwal ................ | C07D 403/06 548/465 |

FOREIGN PATENT DOCUMENTS

| | | | | |
|---|---|---|---|---|
| CN | 101333215 A | 12/2008 | | |
| CN | 101497607 A | 8/2009 | | |
| IN | WO 2010076805 A2 * | 7/2010 | ........... | C07D 403/06 |
| IN | WO 2011058521 A2 * | 5/2011 | ........... | C07D 403/06 |
| WO | WO-2010004339 A1 | 1/2010 | | |
| WO | WO-2010041134 A1 | 4/2010 | | |

OTHER PUBLICATIONS

Lu Kai et al., Improved synthesis of sunitinib malate, Chinese Journal of medicinal Chemistry, 2009, vol. 19, No. 2, p. 116-119.

* cited by examiner

*Primary Examiner* — Nyeemah A Grazier
(74) *Attorney, Agent, or Firm* — Blank Rome LLP

(57) ABSTRACT

The present invention relates to an improved process for the preparation of Sunitinb. The process involves the activation of 5-((Z)-(5-fluoro-2-oxoindolin-3-ylidene) methyl)-2,4-dimethyl-1 H-pyrrole-3carboxylic acid to corresponding suitable carboxylic acid activating group. The present invention also relates to novel acid addition salts of Sunitinb and preparation thereof.

13 Claims, 12 Drawing Sheets

PROCESS FOR THE PREPARATION OF SUNITINIB AND ITS ACID ADDITION SALTS THEREOF

PRIORITY

This application claims the benefit under Indian Provisional Application No. 1083/CHE/2012, filed on Mar. 23, 2012 entitled "An improved process for the preparation of Sunitinib", the contents of which is incorporated by reference herein.

FIELD OF THE INVENTION

The present invention generally relates to an improved process for the preparation of sunitinib and its acid addition salts thereof.

The present invention also relates to novel salts of Sunitinib, processes for their preparation and pharmaceutical compositions containing the same.

BACKGROUND OF THE INVENTION

Sunitinb is chemically described as N-[2-(Diethylamino)ethyl]-5-[(Z)-(5-fluoro-1,2-dihydro-2-oxo-3H-indol-3-ylidene) methyl]-2,4-dimethyl-1H-pyrrole-3-carboxamide as represented by Formula I.

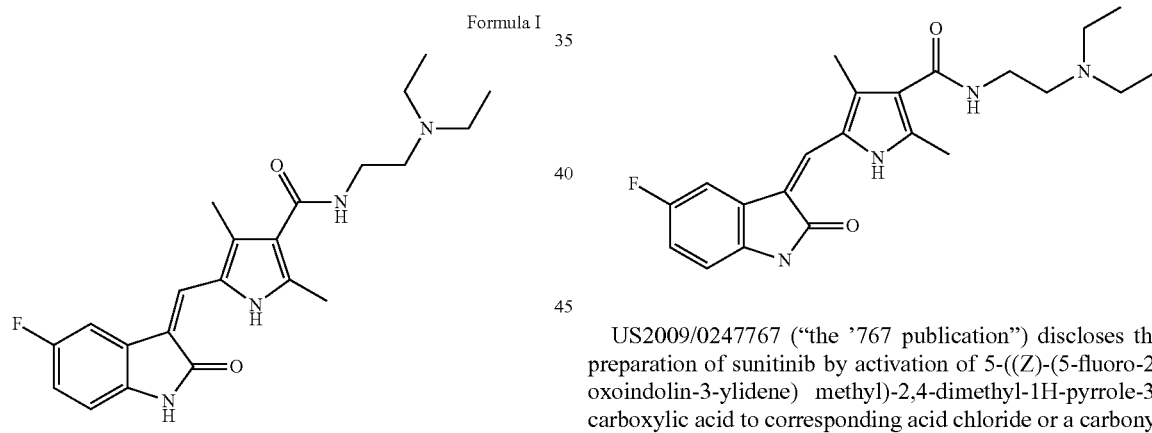

Formula I

Sunitinb (marketed as Sutent by Pfizer) is an oral multi kinase inhibitor and is useful for the treatment of gastrointestinal tumor and advanced renal cell carcinoma. Sunitinb is commercially available as L-malate salt, described as N-[2-(Diethylamino)ethyl]-5-[(Z)-(5-fluoro-1,2-dihydro-2-oxo-3H-indol-3-ylidene) methyl]-2,4-dimethyl-1H-pyrrole-3-carboxamide, (S)-2-hydroxy butanedioic acid (1:1)

Sunitinb and its malate salt are described in corresponding product patent U.S. Pat. No. 6,573,293 ("the '293 patent"), assigned to Sugen and Pharmacia & Upjohn, wherein particular the '293 patent discloses the preparation of sunitinib by the condensation of 5-formyl-2,4-1H-pyrrole-3-carboxylic acid (2-diethylaminoethyl) amide with 5-fluoro 2-oxindole in ethanol in presence of pyrrolidine. The reaction sequence is schematically represented as follows:

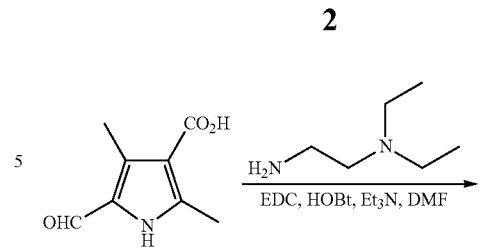

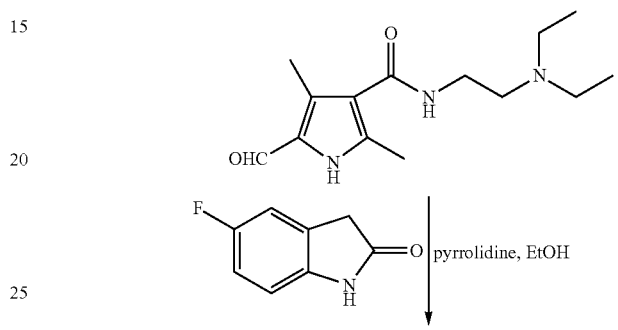

US2009/0247767 ("the '767 publication") discloses the preparation of sunitinib by activation of 5-((Z)-(5-fluoro-2-oxoindolin-3-ylidene) methyl)-2,4-dimethyl-1H-pyrrole-3-carboxylic acid to corresponding acid chloride or a carbonyl dimidazole derivative followed by reaction with 2-diethylaminoethylamine. The reaction sequence is schematically represented as follows:

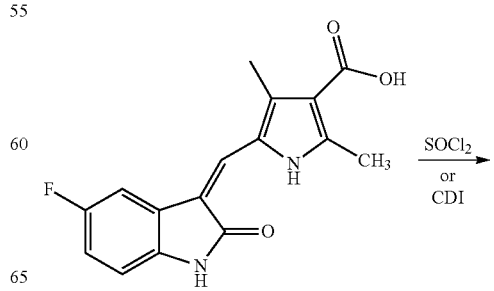

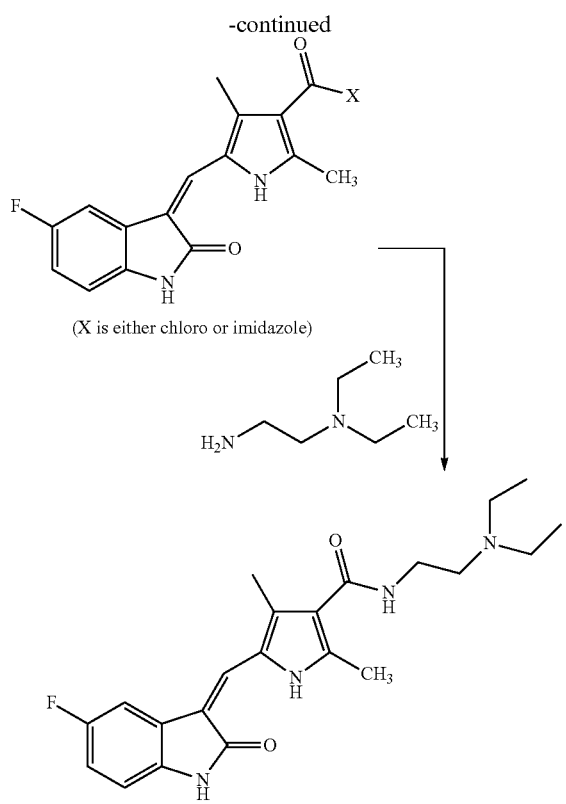

(X is either chloro or imidazole)

The '293 patent discloses salts of sunitinib, such as positively charged moieties including quaternary ammonium, salts such as the hydrochloride, sulfate, carbonate, lactate, tartarate, malate, maleate, succinate; and negatively charged species; however the '293 patent is silent about the preparation and the nature of specific crystal forms of salts.

U.S. Pat. No. 7,435,832 ("the '832 patent") discloses free base and salts of sunitinib (e.g. cyclamic acid, maleic acid, hydrobromic acid, mandelic acid, tartaric acid, fumaric acid, ascorbic acid, phosphoric acid, hydrochloric acid, p-toluenesulfonic acid, citric acid, and malic acid salts) had been screened for properties related to the processing of the salt and the preparation of oral pharmaceutical compositions therefrom, including, for example, crystallinity, toxicity, hygroscopicity, stability, and morphology, but only malate salt was chosen from the screening and only two crystal forms of sunitinib L-malate were specifically disclosed.

PCT publication No. WO 2010/011834 discloses acetate salt of sunitinib and polymorphs thereof.

PCT publication No. WO 2010/041134 discloses the preparation of sunitinib malate through generating a weak acid salt where a weak acid is an acid weaker than malic acid. The weaker acid is preferably described is acetic acid.

PCT publication No. WO 2010/049449 discloses D-tartarate, L-tartarate and citrate salts of sunitinib along with their preparation and corresponding polymorphic forms.

PCT publication No. WO 2011/033472 discloses salt of sunitinib with an achiral acid, wherein achiral acid is selected from the group citric acid, p-toluenesulfonic acid, sulfuric acid, acetic acid and methanesulfonic acid.

PCT Publication No. WO2011/100325 discloses salts of sunitinib and polymorphs thereof such as sunitinib fumarate and sunitinib hydrochloride.

PCT Publication No. WO2012/059941 discloses protic acid salts of sunitinib, wherein the protic acid described is hydrochloride, hydrobromide, phosphate or salicylate.

Salts often improve physical and biological characteristics of without modifying primary pharmacological activity, based on mechanism of action. Thus there is a continuing need to obtain new salts of sunitinib having improved physical or chemical properties.

The present invention satisfies this need by providing new salts of sunitinib with a markedly enhanced solubility in water or aqueous media as an essential property of active pharmaceutical ingredients. The new salt forms or the corresponding polymorphic forms of pharmaceutical product can provide the desirable properties such as handling, increased solubility, increased dissolution, decreased hygroscopicity, stability, storage, shelf life and /or ease to purify.

Since sunitinib constitutes an important therapeutic agent, additional and improved ways for preparing sunitinib and its salts is a great value to pharmaceutical science. Thus there is a need in the development of a consistent and novel and (or) an improved process for preparing sunitinib and its salts which is commercially viable , safer for handing, less time consuming and of greater purity.

The reported methods, involving thionyl chloride associated with certain disadvantages, thionyl chloride is a highly reactive substance, which releases hazardous toxic gases such as sulfur dioxide, sulfur chloride or hydrogen chloride. Moreover the reagent found not to be eco friendly. The other reported process involving the use of carbonyl diimidazole found to be disadvantageous being hygroscopic in nature, which requires highly anhydrous conditions. Thus it provides a scope of an improvement in the process for preparation of sunitinib for industrial scale. In order to overcome the problems associated with the reported procedures, inventors thus designed an improved process for the preparation of sunitinib, suitable for industrial scale with better results in the yield.

SUMMARY OF THE INVENTION

An important aspect of the present invention is an improved process for the preparation of sunitinib through novel activated carboxylic acid intermediates. The present process involves the reaction of 5-((Z)-(5-fluoro-2-oxoindolin-3-ylidene) methyl)-2,4-dimethyl-1H-pyrrole-3-carboxylic acid with a suitable activating group, followed by amidation with N,N-diethyl ethylene diamine to obtain Sunitinb.

In one embodiment, the present invention provides a process for the preparation of sunitinib or its acid addition salts thereof of Formula I, Formula I

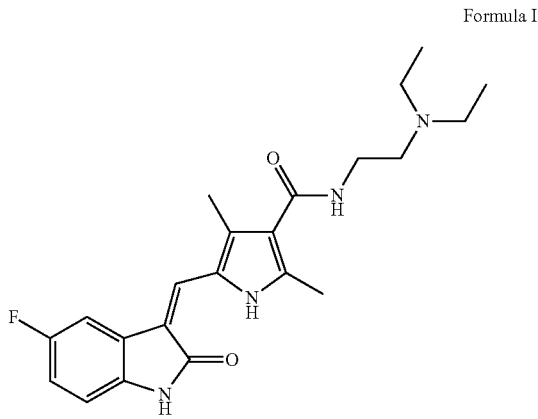 [SMILES: CCN(CC)CCNC(=O)c1c(C)[nH]c(/C=C2\C(=O)Nc3ccc(F)cc32)c1C]

comprising:
a) reacting 5-((Z)-(5-fluoro-2-oxoindolin-3-ylidene) methyl)-2,4-dimethyl-1H-pyrrole-3-carboxylic acid of Formula II

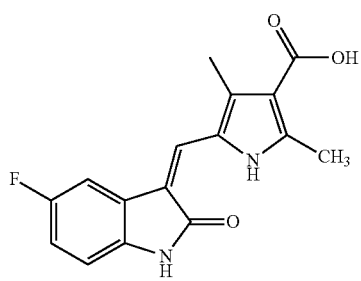

Formula II with a suitable activating agent to obtain an activated compound of Formula III,

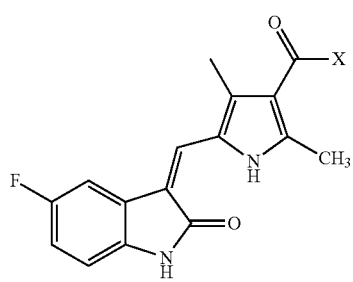

Formula III wherein 'X' represents an activating group, provided 'X' is not chloro or imidazole,
b) amidation of compound of Formula III with N,N-diethyl ethylene diamine in an organic solvent to obtain sunitinib.

In a second embodiment, the present invention provides a process for the preparation of sunitinib or its acid addition salts thereof of Formula I, comprising:
a) reacting 5-((Z)-(5-fluoro-2-oxoindolin-3-ylidene) methyl)-2,4-dimethyl-1H-pyrrole-3-carboxylic acid of Formula II with a suitable sulfonylating agent to obtain an activated compound of Formula III, wherein 'X' represents a sulfonyl group,
b) amidation of compound of Formula III with N,N-diethyl ethylene diamine in an organic solvent to obtain sunitinib.

In a third embodiment, the present invention provides a process for the preparation of compound of Formula III,

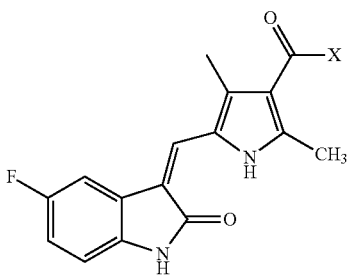

Formula III wherein 'X' represents a sulfonyl group, comprising: reacting 5-((Z)-(5-fluoro-2-oxoindolin-3-ylidene) methyl)-2,4-dimethyl-1H-pyrrole-3-carboxylic acid of Formula II with a suitable sulfonylating agent.

In a fourth embodiment, the present invention provides a compound of Formula III

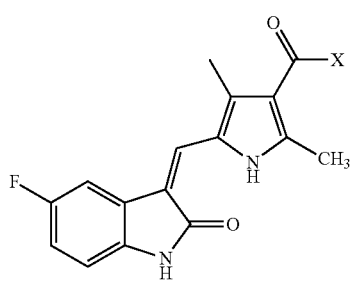

Formula III wherein 'X' represents a sulfonyl group.

In a fifth embodiment, the present invention provides a compound of Formula III, wherein 'X' represents a sulfonyl group selected from sulfonyl compounds such as alkyl or aryl sulfonyl, wherein alkyl represents $C_{1-4}$ linear or branched chain alkyl and aryl represents alkyl substituted or unsubstituted phenyl.

In a sixth embodiment, the present invention provides a compound of Formula III, wherein 'X' represents a p-toluene sulfonyl group.

In a seventh embodiment, the present invention provides a process for the preparation of sunitinib or its acid addition salts thereof of Formula I, comprising:
a) reacting 5-((Z)-(5-fluoro-2-oxoindolin-3-ylidene) methyl)-2,4-dimethyl-1H-pyrrole-3-carboxylic acid of Formula II with p-toluene sulfonyl chloride to obtain p-toluene sulfonyl activated compound of Formula III,
b) amidation of compound of Formula III with N,N-diethyl ethylene diamine in an organic solvent to obtain sunitinib,
c) converting the sunitinib in to its acid addition salts thereof.

In an eighth embodiment, the present invention provides acid addition salts of sunitinib, wherein the acids are selected from the group consisting of malonic acid, oxalic acid, ferulic acid, succinic acid, p-coumaric acid, sinapic acid, caffeic acid, maliec acid, fumaric acid and phosphoric acid.

In a ninth embodiment, the present invention provides sunitinib malonate salt, characterized by an X-ray powder diffraction pattern (XRPD) substantially in accordance with FIG. 2.

In a tenth embodiment, the present invention provides sunitinib oxalate salt, characterized by an X-ray powder diffraction pattern (XRPD) substantially in accordance with FIG. 3.

In an eleventh embodiment, the present invention provides sunitinib ferulate salt, characterized by an X-ray powder diffraction pattern (XRPD) substantially in accordance with FIG. 4.

In a twelfth embodiment, the present invention provides sunitinib succinate salt, characterized by an X-ray powder diffraction pattern (XRPD) substantially in accordance with FIG. 5.

In a thirteenth embodiment, the present invention provides sunitinib p-coumarate salt, characterized by an X-ray powder diffraction pattern (XRPD) substantially in accordance with FIG. 6.

In a fourteenth embodiment, the present invention provides sunitinib sinapate salt, characterized by an X-ray powder diffraction pattern (XRPD) substantially in accordance with FIG. 7.

In a fifteenth embodiment, the present invention provides sunitinib caffeate salt, characterized by an X-ray powder diffraction pattern (XRPD) substantially in accordance with FIG. 8.

In a sixteenth embodiment, the present invention provides sunitinib maleate salt, characterized by an X-ray powder diffraction pattern (XRPD) substantially in accordance with FIG. 9.

In a seventeenth embodiment, the present invention provides sunitinib fumarate salt, characterized by an X-ray powder diffraction pattern (XRPD) substantially in accordance with FIG. 10.

In an eighteenth embodiment, the present invention provides sunitinib phosphate salt (hereinafter referred to as crystalline Form I), characterized by an X-ray powder diffraction pattern (XRPD) substantially in accordance with FIG. 11.

In a nineteenth embodiment, the present invention provides sunitinib phosphate salt (hereinafter referred to as crystalline Form II), characterized by an X-ray powder diffraction pattern (XRPD) substantially in accordance with FIG. 12.

In a twentieth embodiment, the present invention provides a pharmaceutical composition comprising therapeutically effective amount of a sunitinib and its acid addition salts prepared by the processes of the present invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
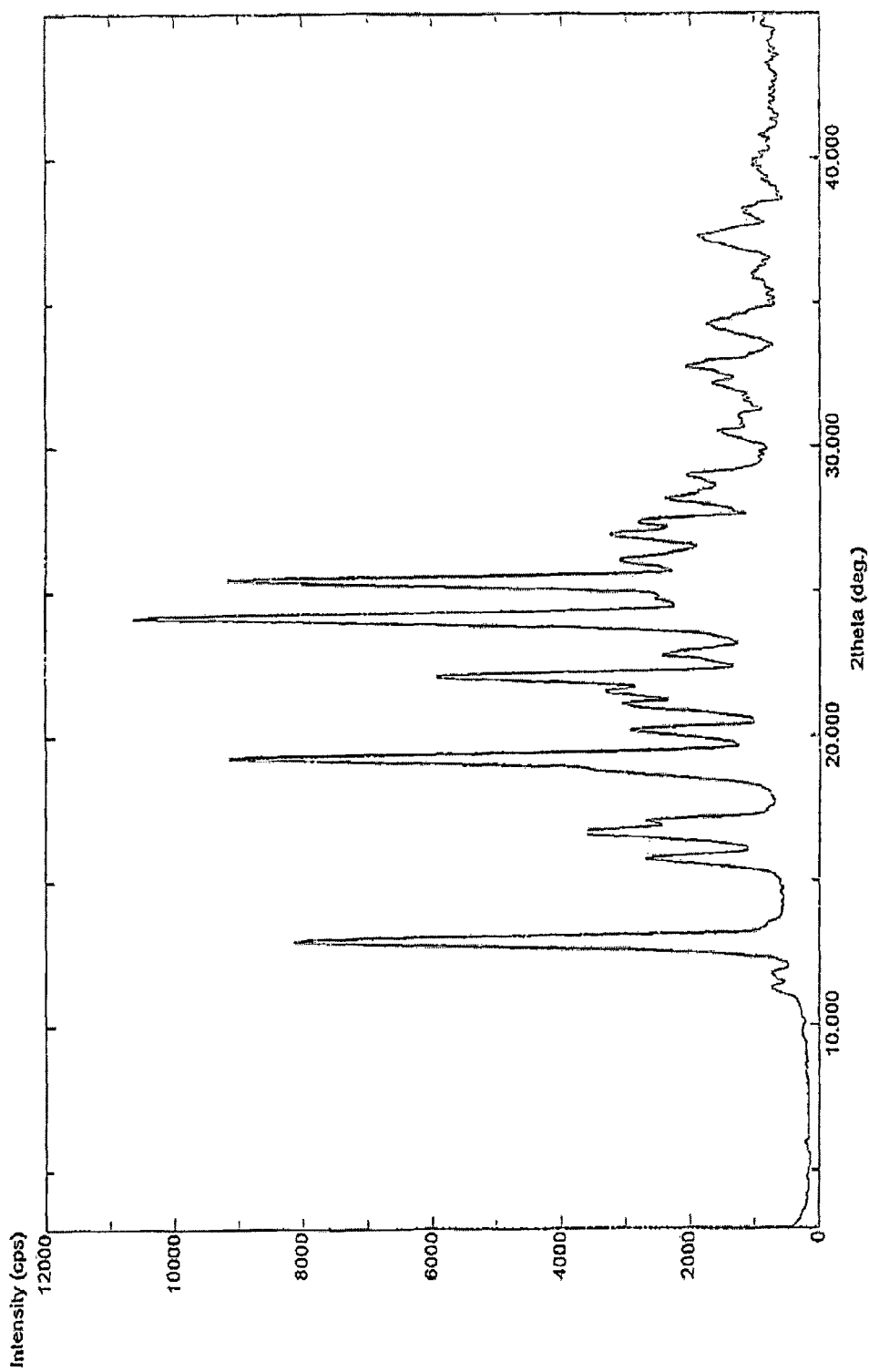
FIG. 1 shows the PXRD pattern of Sunitinib malate

The present invention encompasses an improved process for the preparation of sunitinib through novel activated carboxylic acid intermediates. The present process involves the reaction of 5-((Z)-(5-fluoro-2-oxoindolin-3-ylidene)methyl)-2,4-dimethyl-1H-pyrrole-3-carboxylic acid with a suitable activating group, followed by amidation with N,N-diethyl ethylene diamine to obtain Sunitinb. The present invention also encompasses novel acid addition salts of sunitinib.

In one embodiment, the present invention provides a compound of Formula III

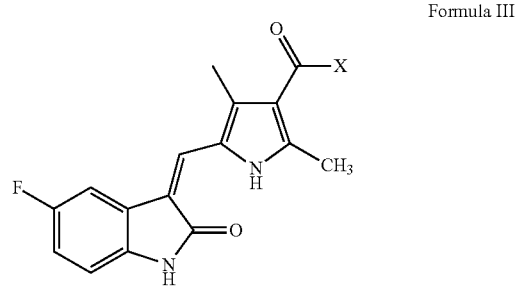

Formula III wherein 'X' represents a sulfonyl group.

In a preferred embodiment, the present invention provides a compound of Formula III, wherein 'X' represents an activating group such as sulfonyl compounds selected from alkyl or aryl sulfonyl, wherein alkyl represents $C_{1-4}$ linear or branched chain alkyl and aryl represents alkyl substituted or unsubstituted phenyl.

In another preferred embodiment, the present invention provides a compound of Formula III, wherein 'X' represents a p-toluene sulfonyl group.

The compound of Formula I can be used to prepare sunitinib and its acid addition salts thereof having the following formula:

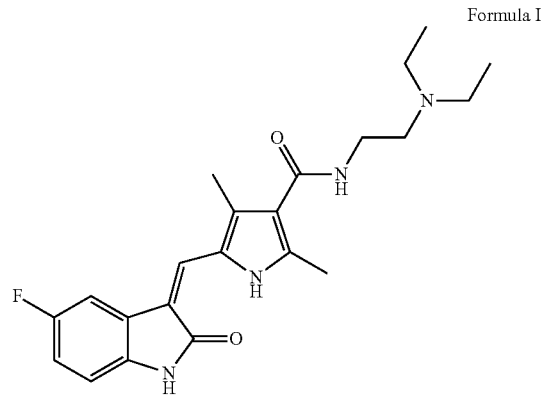 [SMILES: CCN(CC)CCNC(=O)c1c(C)[nH]c(/C=C2\C(=O)Nc3ccc(F)cc32)c1C]

Formula I

In another embodiment, the present invention provides a process for the preparation of sunitinib or its acid addition salts thereof of Formula I, comprising:
a) reacting 5-((Z)-(5-fluoro-2-oxoindolin-3-ylidene)methyl)-2,4-dimethyl-1H-pyrrole-3-carboxylic acid of Formula II

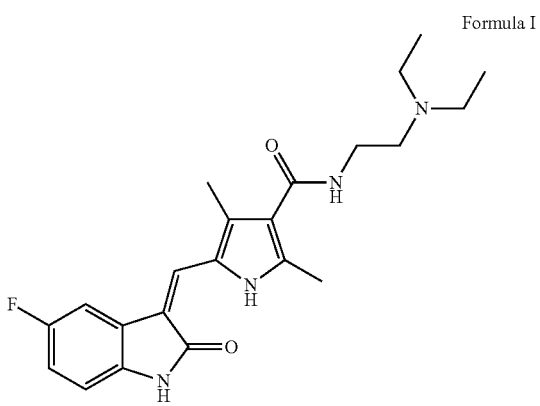 [SMILES: CCN(CC)CCNC(=O)c1c(C)[nH]c(/C=C2\C(=O)Nc3ccc(F)cc32)c1C]
Formula I

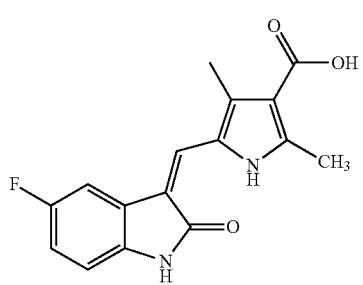
Formula II with a sulfonylating agent to obtain an activated compound of Formula III,

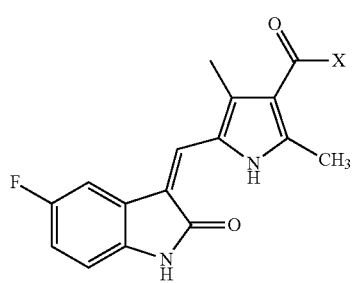
Formula III wherein 'X' represents a sulfonyl group,
b) amidation of compound of Formula III with N,N-diethyl ethylene diamine in an organic solvent to obtain sunitinib.

The reaction of 5-[(Z)-(5-fluoro-2-oxo-1,2-dihydro-3H-indol-3-ylidene)methyl]-2,4-dimethyl-1H-pyrrole-3-carboxylic acid of Formula II with a sulfonylating agent results in the formation of a novel activated carboxylic acid derivative (III), which serve as a purpose of better leaving group. The process with these reagents proved to be faster, facile, a cost effective, proceed with simpler workup procedures with a great improvement in the yields.

The starting material 5-[(Z)-(5-fluoro-2-oxo-1,2-dihydro-3H-indol-3-ylidene)methyl]-2,4-dimethyl-1H-pyrrole-3-carboxylic acid of Formula II is known in the art and can be prepared by any known method, for example starting compound of Formula II may be synthesized as disclosed in U.S. Pat. No. 6,573,293.

Step a) of reaction of Formula II with a sulfonylating agent involves at least one base, an organic solvent and optionally a catalyst.

The suitable sulfonyl group for use herein may be, for example an activating group is sulfonyl compounds. In a preferred embodiment, the sulfonyl compounds such as alkyl or aryl sulfonyl, wherein alkyl represents $C_{1-4}$ linear or branched chain alkyl and aryl represents alkyl substituted or unsubstituted phenyl; more preferably p-toluene sulfonyl.

The sulfonylating agent includes, but is not limited to p-toluene sulfonyl halide such as p-toluene sulfonyl chloride and the like.

A suitable base for use herein may be, for example, an organic base such as a primary, secondary or tertiary amine. Representative examples of such amines include, but are not limited to, triethylamine, tributylamine, diisopropylethylamine, diethylamine, N-methylmorpholine, pyridine, N,N-dimethylaniline, N,N-diethylaniline and the like and mixtures thereof. Alternatively, an inorganic base may be used and includes an alkali metal carbonate such as lithium carbonate, sodium carbonate, potassium carbonate and the like; alkali metal bicarbonate such as lithium bicarbonate, sodium bicarbonate, potassium bicarbonate and the like; alkali metal hydride such as lithium hydride, sodium hydride, potassium hydride and the like; alkali metal hydroxide such as lithium hydroxide, sodium hydroxide, potassium hydroxide and the like; alkali metal alkoxide such as lithium methoxide, sodium methoxide, sodium ethoxide, potassium t-butoxide and the like; and mixtures thereof. The organic amines (particularly pyridine) are preferred.

A suitable catalyst for use herein may be, for example N,N-dimethyl amino pyridine.

The reaction is advantageously carried out in a suitable organic solvent. Suitable organic solvents include, but are not limited to amides such as formamide, dimethylformamide, dimethylacetamide, hexamethylphosphoric triamide and the like and mixtures thereof. Preferably, the suitable organic solvent is dimethyl formamide or dimethyl acetamide being more preferred. In a preferred embodiment of the present invention, the suitable organic solvent is dimethyl formamide. Generally, the amount of organic solvent employed in the reaction can range from about 5 volumes to about 30 volumes and preferably from about 5 volumes to about 20 volumes.

Typically, the reaction is maintained, preferably under stirring to allow the formation of activated compound of Formula III. Preferably, the reaction is maintained for a period of about 1 hour to about 12 hours, more preferably, for about 1 hour to about 3 hours. Preferably, the reaction is maintained at a temperature of less than about room temperature, preferably at about 10° C. to 20° C.

The resultant activated compound of Formula III of the invention can be further processed directly in the same reaction vessel insituly to form sunitinib of Formula I.

Alternatively, the resultant activated compound of Formula III may be isolated from the reaction medium by removing the solvent under vacuum to get the residue by any method known in the art, at the end of the reaction and followed by optional crystallization in to solid compound. The step of concentration may be for example distillation, evaporation, rotational drying (such as with the Buchi Rotavapor), freeze drying, fluidized bed drying, flash drying, spin flash drying, and the like, preferably distillation under vacuum.

The activated compound of Formula III prepared using the process of the present invention can be converted to sunitinib and its acid addition salts thereof, as follows:

Step b) of foregoing process may be carried out by adding sufficient amount of N,N-diethyl ethylene diamine to the resultant product in order to carrying amidation reaction in an organic solvent.

The organic solvent used herein may be include, but are not limited to amides such as formamide, dimethylformamide, dimethylacetamide, hexamethylphosphoric triamide and the like and mixtures thereof. Preferably, the suitable organic solvent is dimethyl formamide or dimethyl acetamide being more preferred. In a preferred embodiment of the present invention, the suitable organic solvent is dimethyl formamide.

Typically, the reaction is maintained, preferably under stirring to allow the formation of sunitinib. Preferably, the reaction is maintained for a period of about 1 hour to about 16 hours, more preferably, for about 1 hour to about 5 hours. Preferably, the reaction is maintained at a temperature of less than 50° C.; more preferably less than about 20° C.

The obtained sunitinib can then be recovered. The recovery process of sunitinib may comprise adding water to the reaction mixture to precipitate sunitinib, filtering off the precipitated sunitinib and drying or optionally extracting the sunitinib from water layer with an organic solvent, for example a water immiscible solvent selected from ethyl acetate, methylene chloride and the like; followed by concentrating the solvent to obtain sunitinib.

In another embodiment of the present invention, sunitinib thus obtained may be purified to minimize the content of des ethyl sunitinib of Formula Id, by dissolving the sunitinib in an organic solvent such as formamide, dimethylformamide, dimethylacetamide, hexamethylphosphoric triamide and the like and mixtures thereof, with dimethylformamide being preferred. The solvent may be heated to obtain a solution at a temperature of from about ambient temperature to about reflux temperature, preferably about 80° C. The reaction solution may be treated with a suitable base and ethyl iodide source.

Formula Id

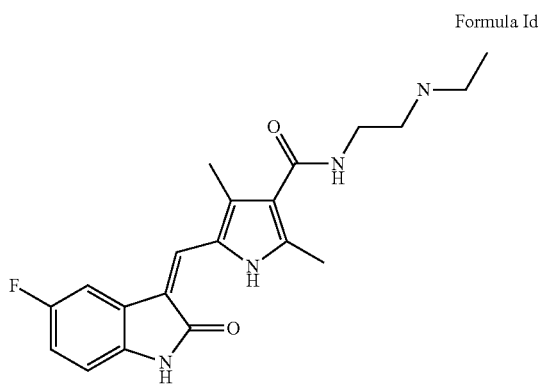 [SMILES: CCNCCNC(=O)c1c(C)[nH]c(/C=C2\C(=O)Nc3ccc(F)cc32)c1C]

The suitable base may be used herein, include any base as described above, with diisopropylethylamine being preferred.

The obtained sunitinib can then be recovered. The recovery process of sunitinib may comprise adding water to the reaction mixture and extracting the sunitinib from water layer with an organic solvent, for example a water immiscible solvent selected from ethyl acetate, methylene chloride and the like; followed by concentrating the solvent to obtain residue, which is further treated with a suitable solvent such as methanol, isopropanol, acetone and the like and mixtures thereof. This may allow for a high purity level of the resulting sunitinib from the crude sunitinib, e.g., a purity of at least about 95% preferably at least about 98% and more preferably at least about 99.5% and less than about 0.1% of des ethyl sunitinib.

The recovered sunitinib can then be converted to sunitinib salt, preferably, to sunitinib malate. The conversion can be done by reacting sunitinib base with an acid, preferably, malic acid. When the acid is malic acid, the conversion can be done, for example, according to the process disclosed in U.S. publication No. 2003/0069298, hereby incorporated by reference.

Alternatively, the recovered sunitinib can then be converted to other pharmaceutically acceptable acid addition salts thereof. The pharmaceutically acceptable acid addition salts include, but are not limited to malonic acid, oxalic acid, ferulic acid, succinic acid, p-coumaric acid, sinapic acid, caffeic acid, maliec acid, fumaric acid and phosphoric acid.

In another embodiment, the present invention provides a process for the preparation of sunitinib acid addition salts thereof, comprising:

a) providing a sunitinib base obtained by the process described above dissolved in one or more organic solvents such as $C_1$ alcohols selected from methanol, ethanol, n-propanol, isopropanol, n-butanol, isobutanol, t-butanol and the like and mixtures thereof; halogenated solvents such as methylene chloride, chloroform and the like and mixtures thereof; nitriles such as acetonitrile, propionitrile, benzonitrile and the like and mixtures thereof; esters such as ethyl acetate, isopropyl acetate and the like and mixtures thereof; ketones such as acetone, methyl ethyl ketone, methyl isobutyl ketone and the like and mixtures thereof; preferably the organic solvents are selected from methanol, isopropanol, acetonitrile, methylene chloride.

b) heating the solution to dissolve the sunitinib free base. Typically, the solution is heated at a temperature of at least about 30° C. to about reflux. Preferably, the solution is heated at about 25° C. to about 85° C., and more preferably at about 25° C. to about 65° C.

c) treating the resultant solution with an acid selected from the group consisting of malonic acid, oxalic acid, ferulic acid, succinic acid, p-coumaric acid, sinapic acid, caffeic acid, maliec acid, fumaric acid and phosphoric acid.

d) isolating the formed sunitinib salts by any conventional techniques, for example concentrated by subjecting the solution to heating, cooling the solution to precipitation, crystallization, solvent precipitation, spray drying, freeze drying, agitated thin film evaporator (ATFE) and the like.

The resultant product may optionally be further dried. Drying can be suitably carried out in a tray dryer, vacuum oven, air oven, fluidized bed drier, spin flash dryer, flash dryer and the like. The drying can be carried out at a temperature ranging from about 30° C. to about 50° C. The drying can be carried out for any desired time until the required product purity is achieved, e.g., a time period ranging from about 1 hour to about 10 hours.

In another embodiment, the present invention provides sunitinib acid addition salts thereof including malate salt prepared using process of the invention having a chemical purity greater than or equal to about 97%, as measured by HPLC, preferably about 98% as measured by HPLC, and more preferably about 99.5%, as measured by HPLC and substantially free of des ethyl sunitinib of Formula Id;

wherein the word "substantially free" refers to sunitinib salts, preferably sunitinib malate salt having less than about 0.1%, of Formula Id, as measured by HPLC, more preferably less than about 0.05% of Formula Id, as measured by HPLC.

In another embodiment, the present invention provides acid addition salts of sunitinib, wherein the acids are selected from the group consisting of malonic acid, oxalic acid, ferulic acid, succinic acid, p-coumaric acid, sinapic acid, caffeic acid, maliec acid, fumaric acid and phosphoric acid.

Figure 2:
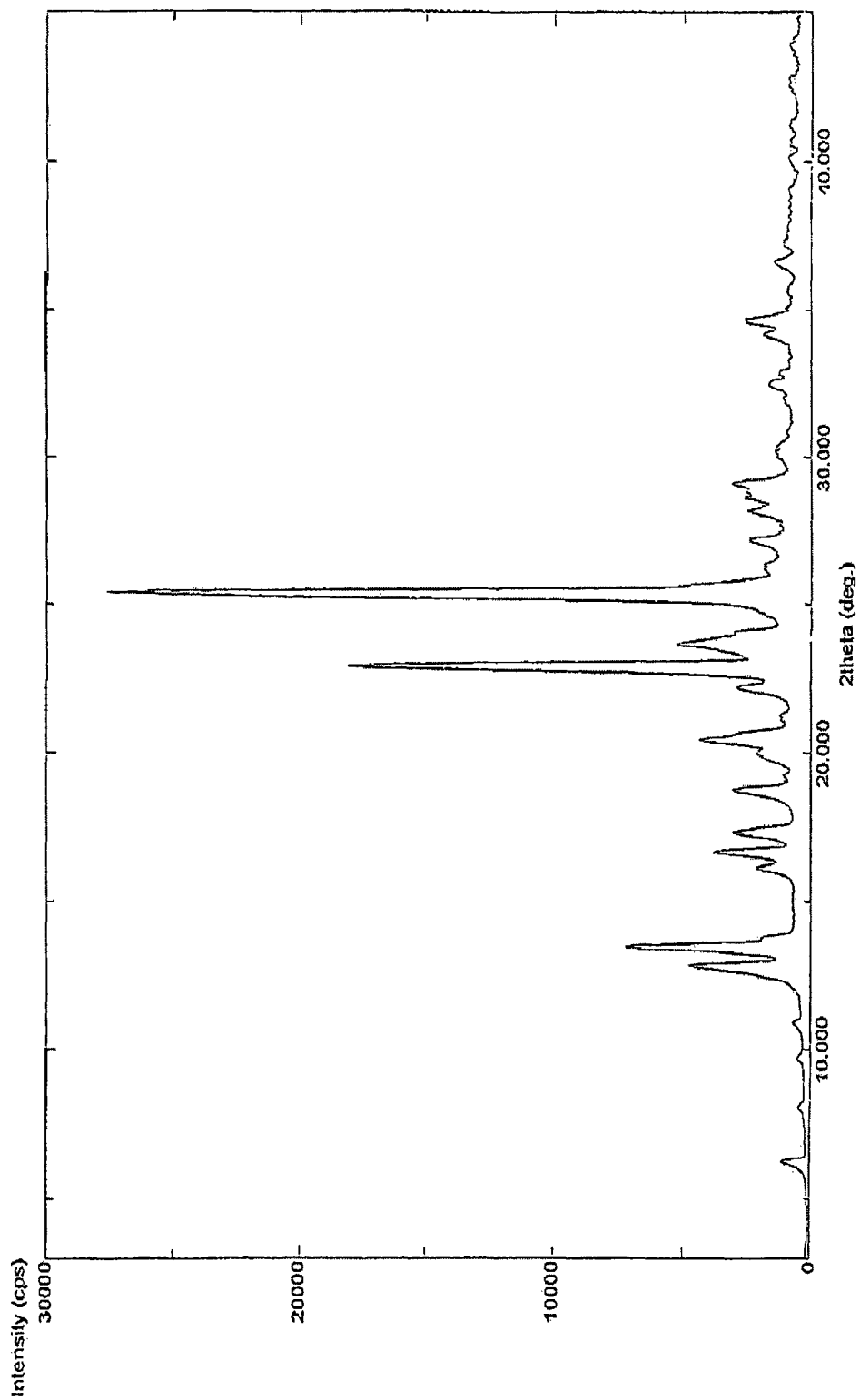
FIG. 2 shows the PXRD pattern of Sunitinib malonate

In another embodiment, the present invention provides sunitinib malonate salt, characterized by an X-ray powder diffraction pattern (XRPD) substantially in accordance with FIG. 2.

Figure 3:
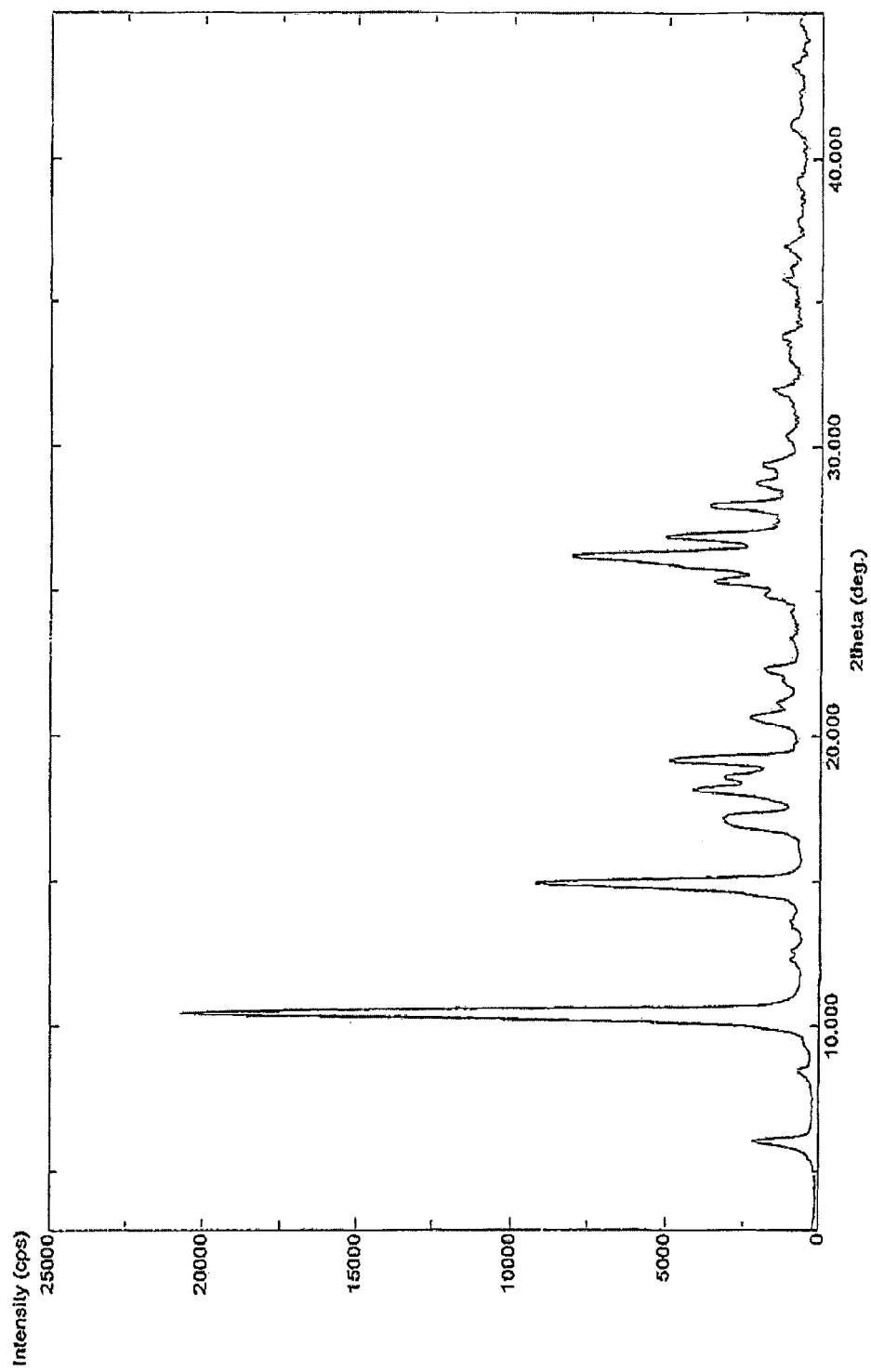
FIG. 3 shows the PXRD pattern of Sunitinib oxalate

In another embodiment, the present invention provides sunitinib oxalate salt, characterized by an X-ray powder diffraction pattern (XRPD) substantially in accordance with FIG. 3.

Figure 4:
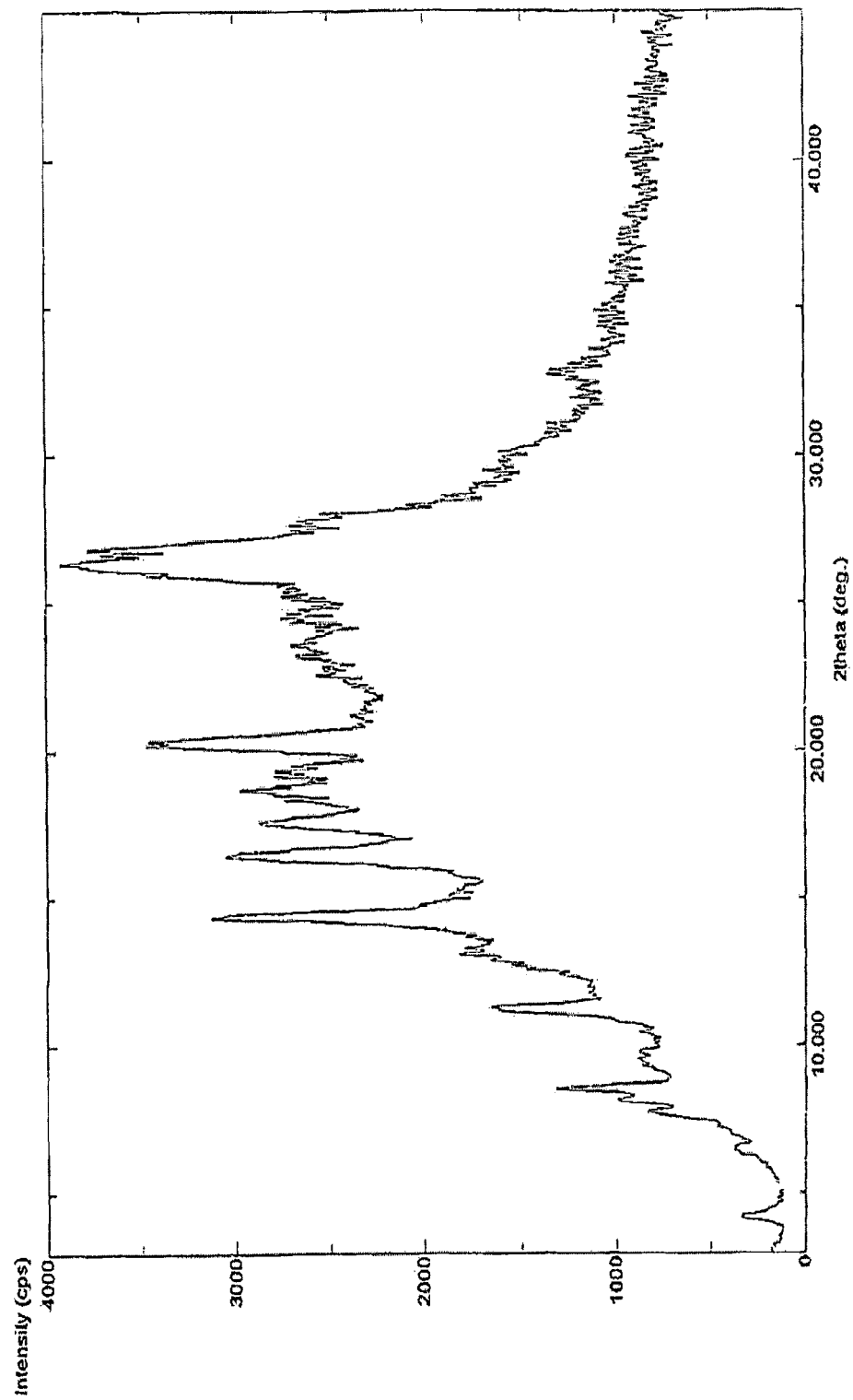
FIG. 4 shows the PXRD pattern of Sunitinib ferulate

In another embodiment, the present invention provides sunitinib ferulate salt, characterized by an X-ray powder diffraction pattern (XRPD) substantially in accordance with FIG. 4.

Figure 5:
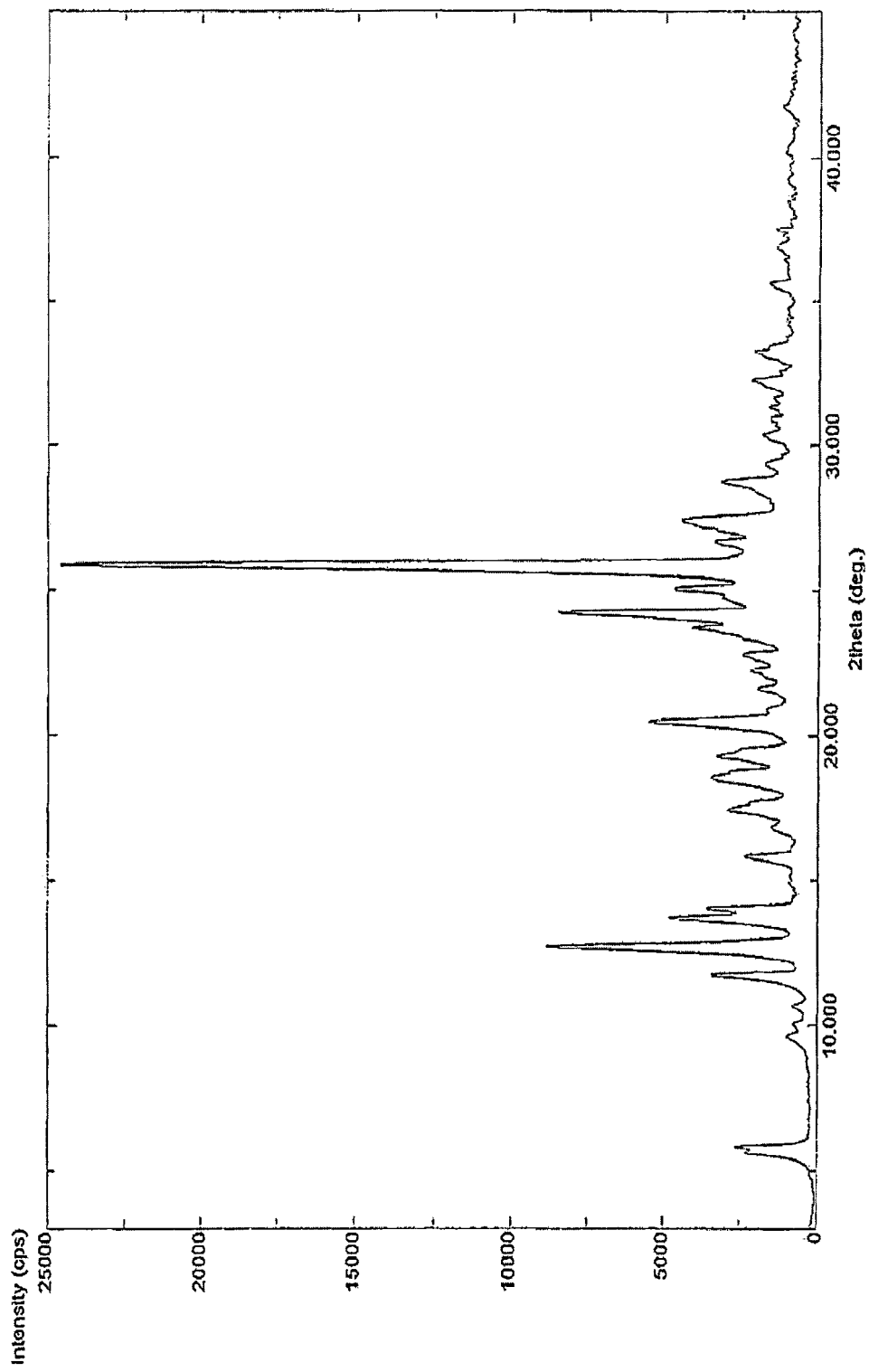
FIG. 5 shows the PXRD pattern of Sunitinib succinate

In another embodiment, the present invention provides sunitinib succinate salt, characterized by an X-ray powder diffraction pattern (XRPD) substantially in accordance with FIG. 5.

Figure 6:
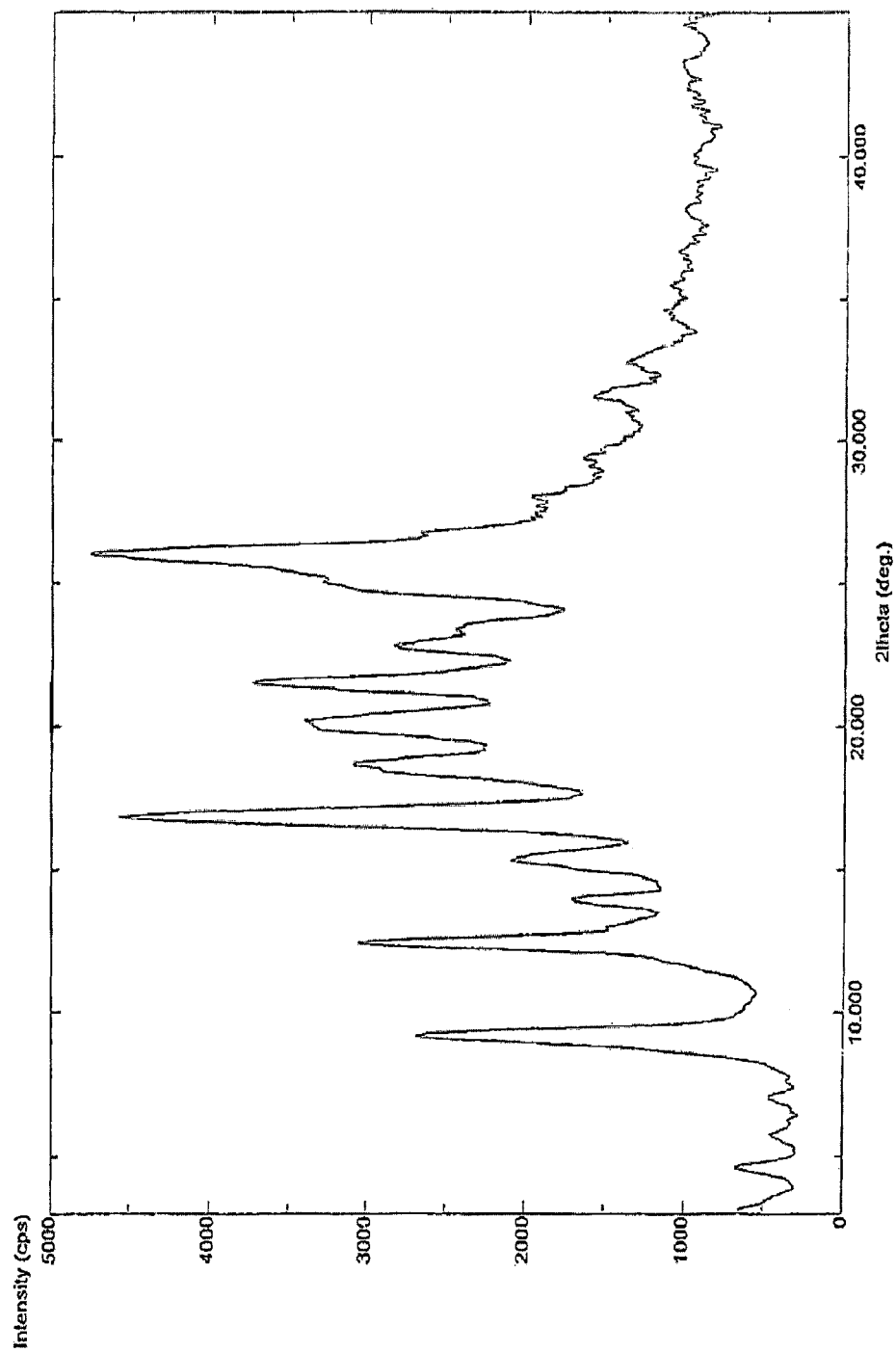
FIG. 6 shows the PXRD pattern of Sunitinib coumarate

In another embodiment, the present invention provides sunitinib p-coumarate salt, characterized by an X-ray powder diffraction pattern (XRPD) substantially in accordance with FIG. 6.

Figure 7:
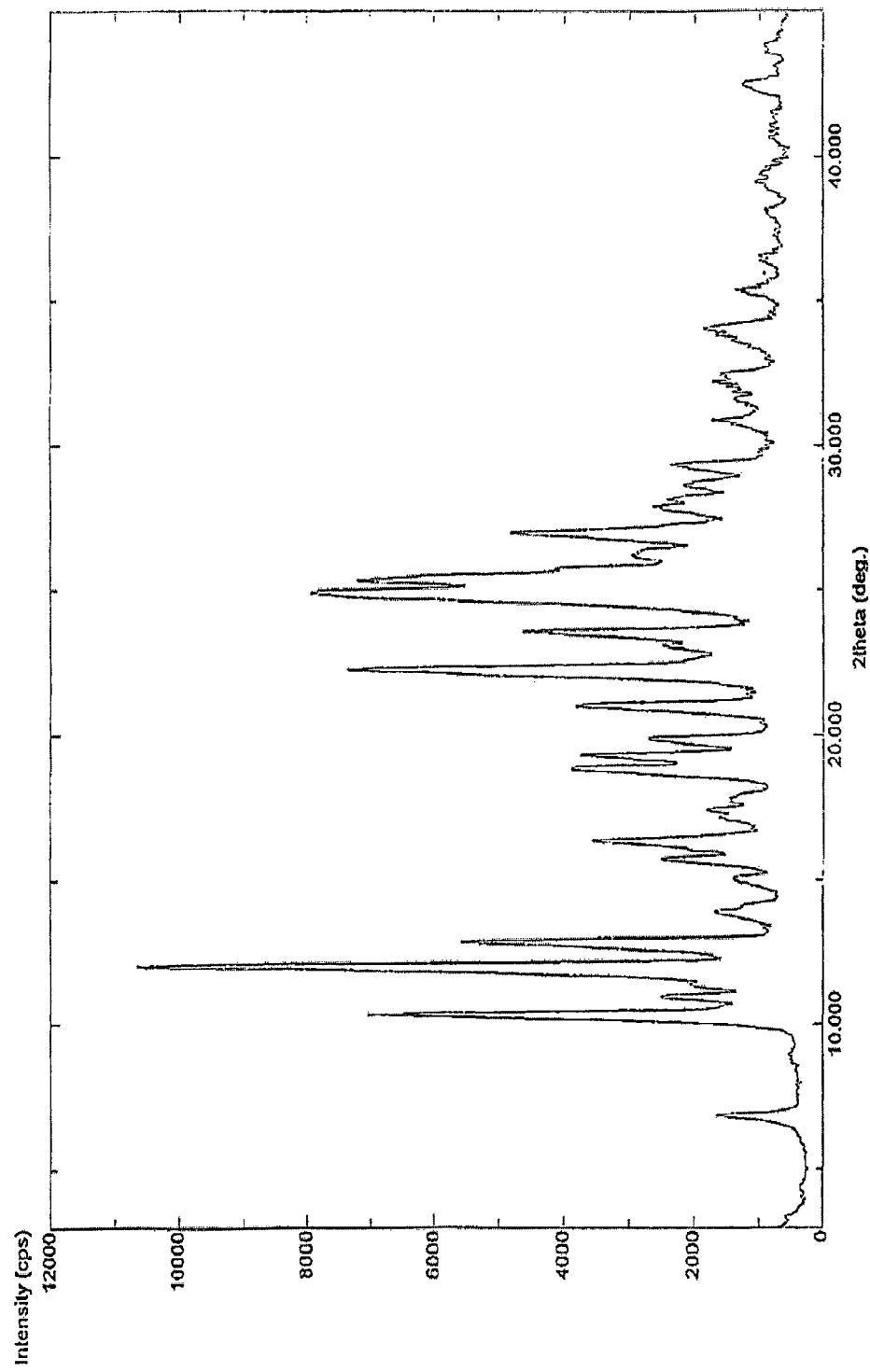
FIG. 7 shows the PXRD pattern of Sunitinib sinapinate

In another embodiment, the present invention provides sunitinib sinapate salt, characterized by an X-ray powder diffraction pattern (XRPD) substantially in accordance with FIG. 7.

Figure 8:
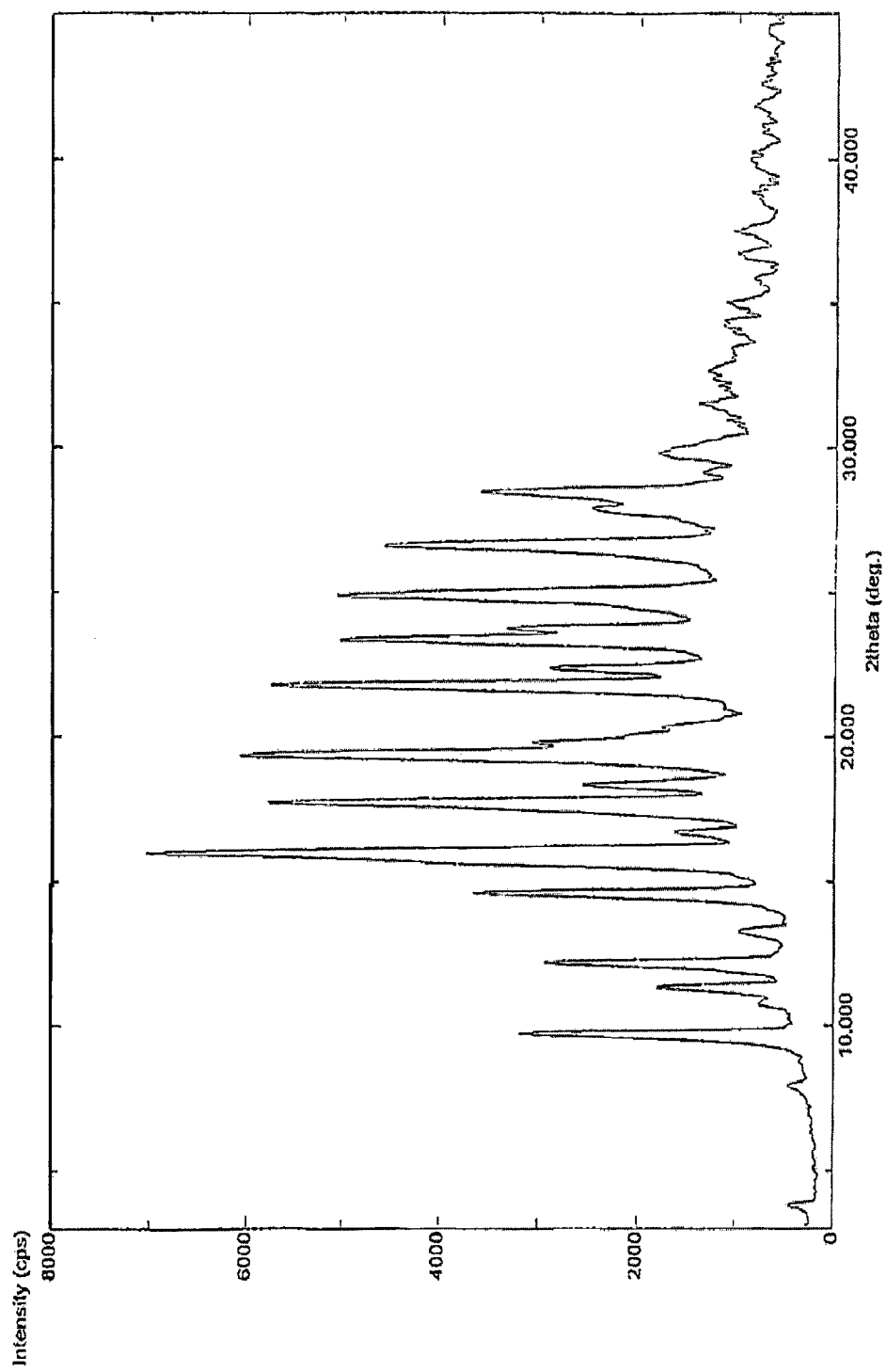
FIG. 8 shows the PXRD pattern of Sunitinib caffeate

In another embodiment, the present invention provides sunitinib caffeate salt, characterized by an X-ray powder diffraction pattern (XRPD) substantially in accordance with FIG. 8.

Figure 9:
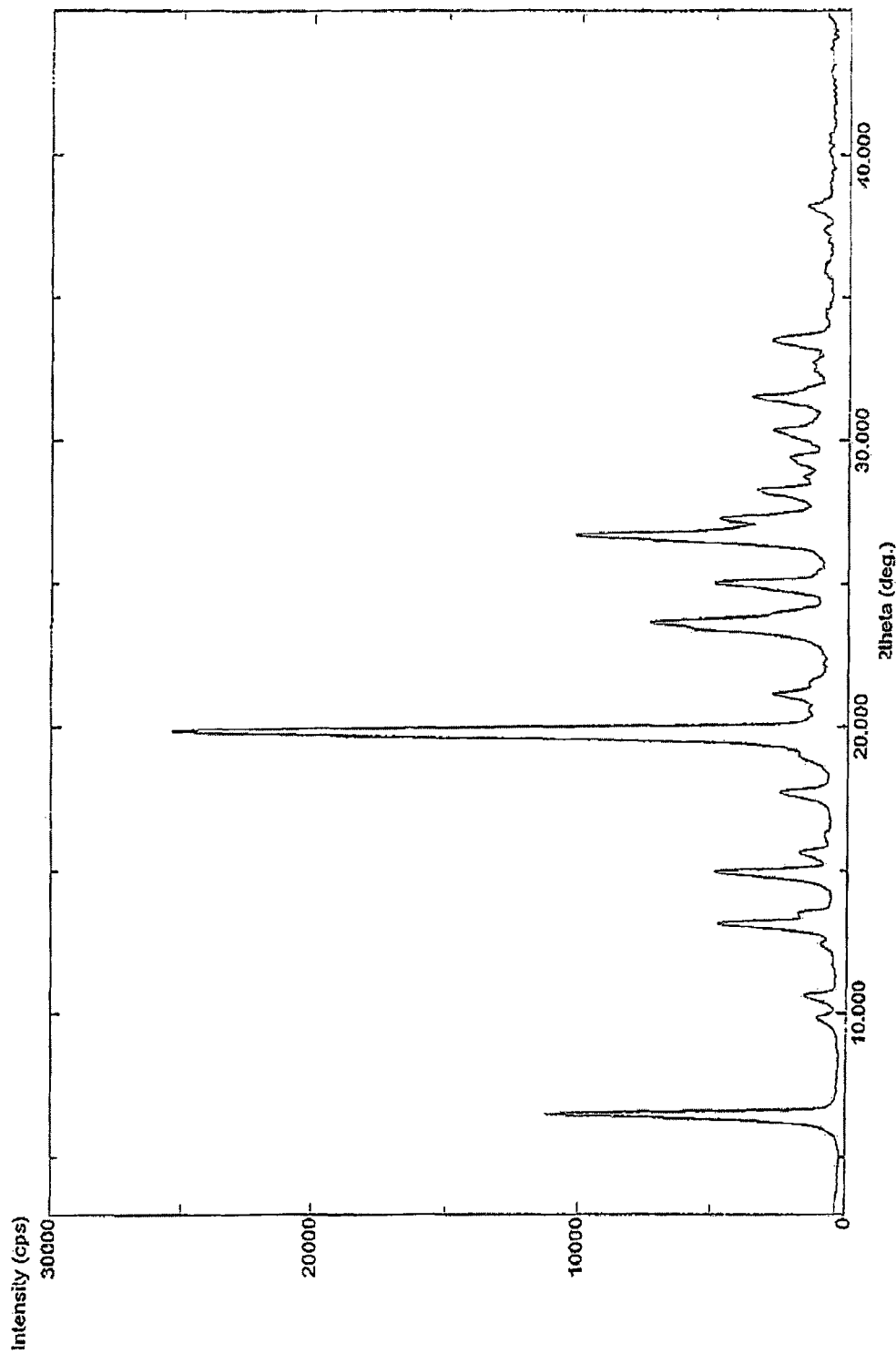
FIG. 9 shows the PXRD pattern of Sunitinib maleate

In another embodiment, the present invention provides sunitinib maleate salt, characterized by an X-ray powder diffraction pattern (XRPD) substantially in accordance with FIG. 9.

Figure 10:
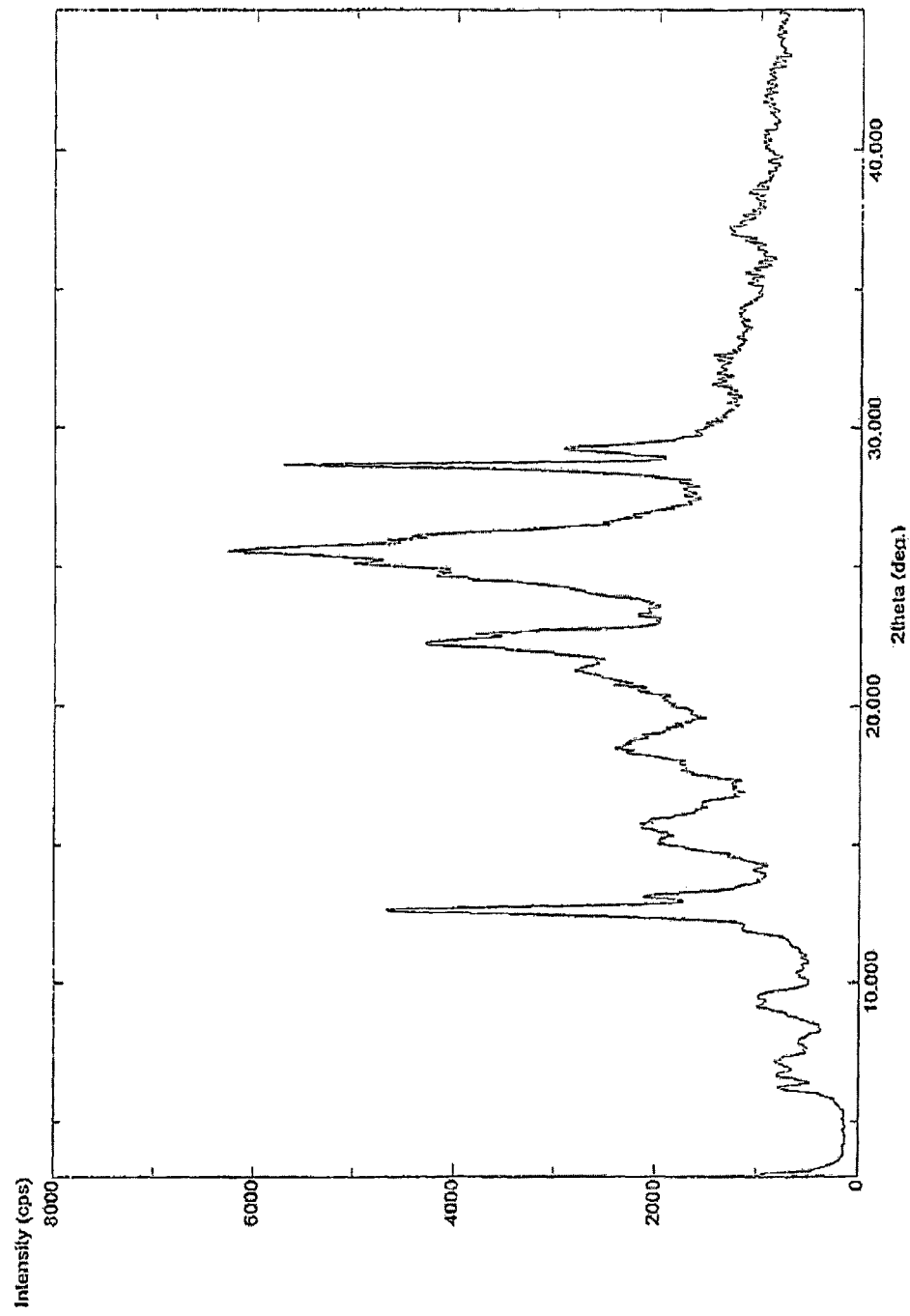
FIG. 10 shows the PXRD pattern of Sunitinib fumarate

In another embodiment, the present invention provides sunitinib fumarate salt, characterized by an X-ray powder diffraction pattern (XRPD) substantially in accordance with FIG. 10.

In another embodiment, the present invention provides sunitinib phosphate salt (hereinafter referred to as crystalline Form I), characterized by an X-ray powder diffraction pattern (XRPD) substantially in accordance with FIG. 11.

In another embodiment, the present invention provides sunitinib phosphate salt (hereinafter referred to as crystalline Form II), characterized by an X-ray powder diffraction pattern (XRPD) substantially in accordance with FIG. 12.

In one preferred embodiment of the invention, sunitinib is prepared according to Scheme I:

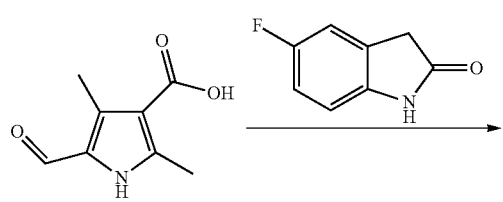

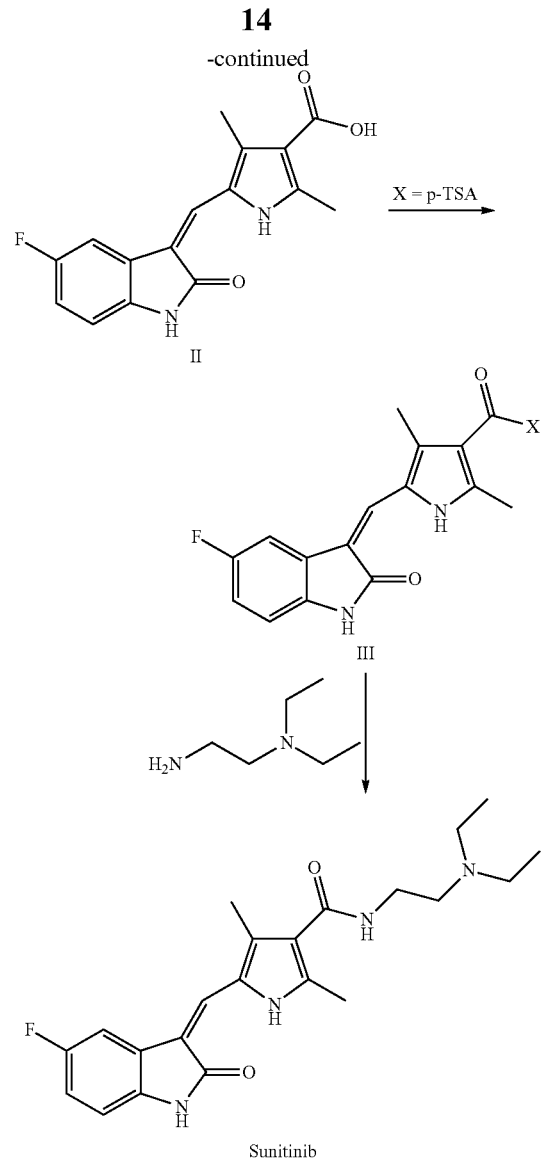

In another embodiment, sunitinib acid addition salts thereof of the present invention characterized by X-ray powder diffraction (XRD) pattern. The X-Ray powder diffraction can be measured by an X-ray powder diffractometer equipped with a Cu-anode ([λ]=1.54 Angstrom), X-ray source operated at 30 kV, 15 mA and a Ni filter is used to strip K-beta radiation. Two-theta calibration is performed using an NIST SRM 640c Si standard. The sample was analyzed using the following instrument parameters: measuring range=3-45°2θ; step width=0.020°; and scan speed=5°/minute.

EXAMPLES

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Example 1

Preparation of Sunitinib Base

A mixture of 5-((Z)-(5-fluoro-2-oxoindolin-3-ylidene)methyl)-2,4-dimethyl-1H-pyrrole-3-carboxylic acid (70 g) in DMF (1050 mL) was cooled to 15-19° C. To this mixture p-toluene sulfonyl chloride (133.4 g) in DMF (350 mL) was added in 15 min. 4-dimethylamino pyridine (81.3 g) in DMF (350 mL) was added in 15 min and pyridine (36.9 g) was added in 15 min at 15-19° C. The reaction mixture was stirred at the same temperature over a period of 60-90 minutes. The reaction mass was cooled to 13-16° C. To the above reaction mixture N, N-diethyl ethylene diamine (81.3 g) in DMF (350 mL) was added in 10 min at 13-16° C. The reaction mass was maintained under stirring for a period of 30 minutes at the same temperature. The progress of the rection was monitored by HPLC with a limit of 5-((Z)-(5-fluoro-2-oxoindolin-3-ylidene)methyl)-2,4-dimethyl-1H-pyrrole-3-carboxylic acid not more than 5.0%. After the completion of reaction 28 mL of water was charged and DMF was distilled off under vacuum. 1050 mL of 5% sodium bicarbonate solution was charged under stirring. The pH of the above solution was adjusted to 12-13 by 50% NaOH solution. Ethyl acetate was charged and it was stirred for 5 min. The organic layer were separated and treated with 1% NaOH, and brine solution followed by separation of the ethyl acetate fraction and distillation off under vacuum below 50° C. The residue was treated with 30% methanol in water to isolate the material. It was treated with methanol to obtain sunitinib base. The obtained solid was dried under vacuum at 55-65° C. over for a period of 5 hrs. Yield: 65.6 g of Sunitinib base with ~0.5% des ethyl sunitinib.

Example 2

Purification of Sunitinib Base

Sunitinib obtained in above reaction (with ~0.5% des ethyl sunitinib) was dissolved in DMF at room temperature and heated to 80° C. to obtain a clear solution. The temperature of the system was cooled down to 15-20° C. in 30 minutes period followed by the addition of diisopropyl ethyl amine (5.32 g) over 10 min. The reaction mass was maintained over 15 min period under stirring and ethyl iodide (6.43 g) was added over 15 min period. The reaction mass was stirred over 8 hrs period at room temperature and the progress of the reaction was monitored by HPLC (des ethyl impurity content NMT 0.1%). After the completion of reaction (1640 mL) 5% sodium bicarbonate solution,(262 mL) 50% NaOH and ethyl acetate were added. The organic fraction was separated and treated with water and brine solution.The ethyl acetate fraction was separated and distilled off to obtain the residue. The residue was treated with methanol to get crude sunitinib base. The above crude was treated with acetone. The solid obtained was filtered and dried under vacuum over 5 hr period at 55-60° C. to obtain sunitinib (48 g, less than 0.1% des ethyl sunitinib)

Example 3

Preparation of Sunitinib L-malate

Sunitinib (10 g) was suspended in methanol (1540 mL) under stirring and L-malic acid (3.36 g) was added to it at a temperature 25-30° C. The reaction mass was stirred to get a clear solution. It was filtered and methanol was distilled off under vacuum below 40° C. Acetonitrile (50 mL) was charged and the solvent was distilled off. It was cooled to 25-30° C. 380 mL of acetonitrile was added to the mass and it was mentained at 45-50° C. under stirring for a period of 15 minutes. The reaction mass was cooled to 30-35° C. The solid obtained was filtered and washed with acetonitrile (10 mL). The resultant compound was suck dried and dried under vacuum over a period of 4-5 hrs at 50° C. to obtain sunitinib L-malate. (12.0 g; yield 90%)

Purity by HPLC: 98.5%; L-malic acid content: 24-26% (w/w);

DSC: onset 195° C. and endset 198.77° C.; TGA: No loss observed till 200° C.;

Moisture content: 0.79%

IR (cm$^{-1}$): 3328, 3233, 3073, 2984, 2885, 1673, 1635, 1574, 1529, 1496, 1477, 1439, 1322, 1278, 1256, 1196, 807, 791

The XRPD is set forth in FIG. 1.

Example 4

Preparation of Sunitinib Malonate

Sunitinib (2.0 g) was suspended in 10% methanol in dichloromethane (30 mL) at 25° C., followed by addition of malonic acid (0.29 g). The reaction mass was maintained under stirring at 25-30° C. for 15 hrs. The solids obtained were filtered, suck dried and dried under vacuum for a period of 10 hrs at 60° C. to obtain sunitinib malonate. (2.0 g; yield: 80%)

Purity by HPLC: 99.86%; malonic acid content-20.49% (w/w);

DSC: onset 178° C. and endset 182° C.; TGA: 0.27%;

IR (in cm$^{-1}$): 3434, 3214, 1676, 1643, 1587, 1532, 1478, 1437, 1367, 1322, 1284, 1258, 1222, 1195, 1176, 1143, 1095, 1046, 956, 921, 865, 848, 824, 792, 696, 665, 607, 597, 585, 553

The XRPD is set forth in FIG. 2.

Example 5

Preparation of Sunitinib Oxalate:

Sunitinib (1.0 g) was suspended in 10% methanol in dichloromethane (30mL) at 25° C., followed by addition of oxalic acid (0.22 g). The reaction mass was maintained under stirring at 25-30° C. for 60 minutes. The solids obtained were filtered, suck dried and dried under vacuum for a period of 10 hrs at 60° C. to obtain sunitinib malonate. (0.9 g; yield: 75%)

Purity by HPLC: 99.67%; oxalic acid content: 19.24% (w/w)

DSC: onset peak 250° C. and endset peak at 254° C.

TGA: 0.1-3.2%

IR (in cm$^{-1}$):3230, 3044, 2981, 1677, 1615, 1589, 1522, 1478, 1447, 1400, 1326, 1287, 1280, 1261, 1231, 1197, 1172, 1161, 1142, 1054, 1036, 971, 923, 900, 840, 819, 777, 755, 690.

The XRPD is set forth in FIG. 3.

Example 6

Preparation of Sunitinib Ferulate

Sunitinib (1.0 g) was suspended in methanol (152 mL), followed by addition of ferulic acid (0.48 g) at 25-35° C. over a period of 15 minutes. After the stipulated time period, methanol was completely distilled off under vacuum below 45° C. The residue was treated with acetonitrile (38 mL) and refluxed. The reaction mass was maintained at reflux temperature for 60 minutes. The reaction mass was cooled to 25-35° C. for crystallization. The solid obtained was filtered, washed with acetonitrile, suck dried and dried under vacuum at 60° C. over 4-5 hr period to obtain sunitinib ferulate. (1.2 g; yield:81%)

Purity by HPLC: 99.62%; ferulic acid content: 31.78% (w/w);

TGA: 1%; DSC: 132-138° C.; 192-193° C.; 203-212° C.

IR (in cm$^{-1}$): 3367, 3228, 3043, 2971, 2934, 1680, 1633, 1587, 1515, 1479, 1428, 1375, 1327, 1280, 1261, 1232, 1197, 1147, 1124, 1029, 979, 925, 843, 811, 793, 775, 700, 669.

The XRPD is set forth in FIG. 4.

Example 7

Preparation of Sunitinib Succinate

Sunitinib (1.0 g) was suspended in methanol (152 mL), followed by addition of succinic acid (0.29 g) at 25-35° C. over a period of 15 minutes. After the stipulated time period, methanol was completely distilled off under vacuum below 45° C. The residue was treated with acetonitrile (38 mL) and refluxed. The reaction mass was maintained at reflux temperature for 60 minutes. The reaction mass was cooled to 25-35° C. for crystallization. The solid obtained was filtered, washed with acetonitrile, suck dried and dried under vacuum at 60° C. over 4-5 hr period to obtain sunitinib ferulate. (1.1 g; yield:85%)

Purity by HPLC: 99.74%; succinic acid content: 21.56% (w/w);

TGA: Nil; DSC: onset peak at 193° C. and end set peak at 200° C.

IR (in cm$^{-1}$): 3386, 3232, 2972, 1680, 1630, 1581, 1525, 1495, 1478, 1440, 1394, 1326, 1289, 1259, 1230, 1196, 1145, 1096, 1048, 877, 809, 794, 697, 666, 607, 586

The XRPD is set forth in FIG. 5.

Example 8

Preparation of Sunitinib Coumarate

Sunitinib (1.0 g) was suspended in methanol (152 mL), followed by addition of coumaric acid (0.41 g) at 25-35° C. over a period of 15 minutes. After the stipulated time period, methanol was completely distilled off under vacuum below 45° C. The residue was treated with acetonitrile (38 mL) and refluxed. The reaction mass was maintained at reflux temperature for 60 minutes. The reaction mass was cooled to 25-35° C. for crystallization. The solid obtained was filtered, washed with acetonitrile, suck dried and dried under vacuum at 60° C. over 4-5 hr period to obtain sunitinib coumarate.(1.1 g; yield:78%)

Purity by HPLC: 99.51%; coumaric acid content: 23.13% (w/w);

TGA: Nil; DSC: 115-121° C.; 134-140° C.; 207-219° C.

IR (in cm$^{-1}$) 3430, 3216, 2974, 1676, 1635, 1588, 1543, 1513, 1478, 1375, 1328, 1282, 1258, 1196, 1168, 1148, 983, 836, 798, 669, 613, 586

The XRPD is set forth in FIG. 6.

Example 9

Preparation of Sunitinib Sinapate

Sunitinib (1.0 g) was suspended in methanol (152 mL), followed by addition of sinapic acid (0.56 g) at 25-35° C. over a period of 15 minutes. After the stipulated time period, methanol was completely distilled off under vacuum below 45° C. The residue was treated with acetonitrile (38 mL) and refluxed. The reaction mass was maintained at reflux temperature for 60 minutes. The reaction mass was cooled to 25-35° C. for crystallization. The solid obtained was filtered, washed with acetonitrile, suck dried and dried under vacuum at 60° C. over 4-5 hr period to obtain sunitinib sinapinate.(1.3 g; yield:83%)

Purity by HPLC: 99.82%; sinapic acid content: 36.92% (w/w);

TGA: Nil; DSC: onset peak at 170° C. and endset peak at 175° C.

IR (in cm$^{-1}$): 3327, 3232, 2983, 2884, 2697, 1673, 1634, 1573, 1528, 1477, 1440, 1422, 1384, 1361, 1321, 1293, 1278, 1255, 1229, 1195, 1160, 1147, 1103, 1027, 960, 921, 909, 891, 863, 806, 791, 770, 737, 709, 694, 664, 653, 605, 586, 532.

The XRPD is set forth in FIG. 7.

Example 10

Preparation of Sunitinib Caffeate

Sunitinib (1.0 g) was suspended in methanol (152 mL), followed by addition of caffeic acid (0.45 g) at 25-35° C. over a period of 15 minutes. After the stipulated time period, methanol was completely distilled off under vacuum below 45° C. The residue was treated with acetonitrile (38 mL) and refluxed. The reaction mass was maintained at reflux temperature for 60 minutes. The reaction mass was cooled to 25-35° C. for crystallization. The solid obtained was filtered, washed with acetonitrile, suck dried and dried under vacuum at 60° C. over 4-5 hr period to obtain sunitinib caffeate. (1.3 g; yield:89%)

Purity by HPLC: 99.06%; caffeic acid content: 30.48% (w/w);

TGA: 0.29%; DSC: 157-163° C.; 190-198° C.; 211-214° C.

IR (in cm$^{-1}$): 3402, 3201, 2980, 1668, 1627, 1574, 1525, 1480, 1443, 1382, 1355, 1328, 1293, 1280, 1257, 1231, 1193, 1164, 1149, 1121, 1096, 1071, 1051, 1034, 1014, 982, 917, 860, 823, 793, 773, 719, 666, 608, 586.

The XRPD is set forth in FIG. 8.

Example 11

Preparation of Sunitinib Maleate

Sunitinib (2.0 g) was suspended in 10% methanol in dichloromethane at 25° C. , followed by addition of maleic acid (0.58 g) .The reaction mass was maintained under stirring at 25-30° C. for 60 minutes. The solids obtained were filtered, suck dried and dried under vacuum for a period of 10 hrs at 60° C. to obtain sunitinib maleate. (2.3 g; yield: 89%)

Purity by HPLC: 99.59%; maleic acid content: 22.34% (w/w);

TGA: 0.16%; DSC: onset 208.7° C. and end set: 212.7° C.

IR (in cm$^{-1}$): 3421, 3175, 1678, 1626, 1575, 1528, 1468, 1445, 1382, 1349, 1327, 1290, 1259, 1195, 1149, 864, 822, 791, 697, 668, 611, 591.

The XRPD is set forth in FIG. 9.

Example 12

Preparation of Sunitinib Fumarate

Sunitinib (1.0g) was suspended in methanol (152 mL), followed by addition of fumaric acid (0.29 g) at 25-35° C.

over a period of 15 minutes. After the stipulated time period, methanol was completely distilled off under vacuum below 45° C. The residue was treated with acetonitrile (38 mL) and refluxed. The reaction mass was maintained at reflux temperature for 60 minutes. The reaction mass was cooled to 25-35° C. for crystallization. The solid obtained was filtered, washed with acetonitrile, suck dried and dried under vacuum at 60° C. over 4-5 hr period to obtain sunitinib fumarate.(1.2 g; yield: 93%)

Purity by HPLC: 99.69%; fumaric acid content: 29.20% (w/w);

TGA: 1.3%; DSC: 110-119° C.; 164-176° C.

IR (in cm$^{-1}$): 3431, 3156, 3085, 3042, 2946, 2880, 1671, 1634, 1577, 1547, 1521, 1480, 1374, 1331, 1279, 1264, 1241, 1214, 1200, 1167, 1148, 1100, 1029, 982, 927, 912, 852, 795, 724, 696, 670, 646, 636, 616, 585, 518.

The XRPD is set forth in FIG. 10.

Example 13

Preparation of Sunitinib Phosphate Form I

Sunitinib (1.0 g) was suspended in methanol (152 mL), followed by addition of phosphoric acid (0.24 g) at 25-35° C. over a period of 15 minutes. After the stipulated time period, methanol was completely distilled off under vacuum below 45° C. The residue was treated with acetonitrile (38 mL) and refluxed. The reaction mass was maintained at reflux temperature for 60 minutes. The reaction mass was cooled to 25-35° C. for crystallization. The solid obtained was filtered, washed with acetonitrile, suck dried and dried under vacuum at 60° C. over 4-5 hr period to obtain sunitinib phosphate. (1.18 g; yield: 95%)

Purity by HPLC: 99.45%; phosphoric acid content: 19.10% (w/w)

TGA: 0.1%; DSC: onset peak 266° C. and end set at 271° C.

IR (in cm$^{-1}$): 3377, 3188, 3068, 2984, 1670, 1637, 1578, 1538, 1480, 1445, 1401, 1387, 1369, 1325, 1292, 1277, 1257, 1229, 1195, 1147, 1129, 1092, 1049, 947, 862, 827, 797, 781, 745, 719, 696, 665, 606, 585, 521.

Figure 11:
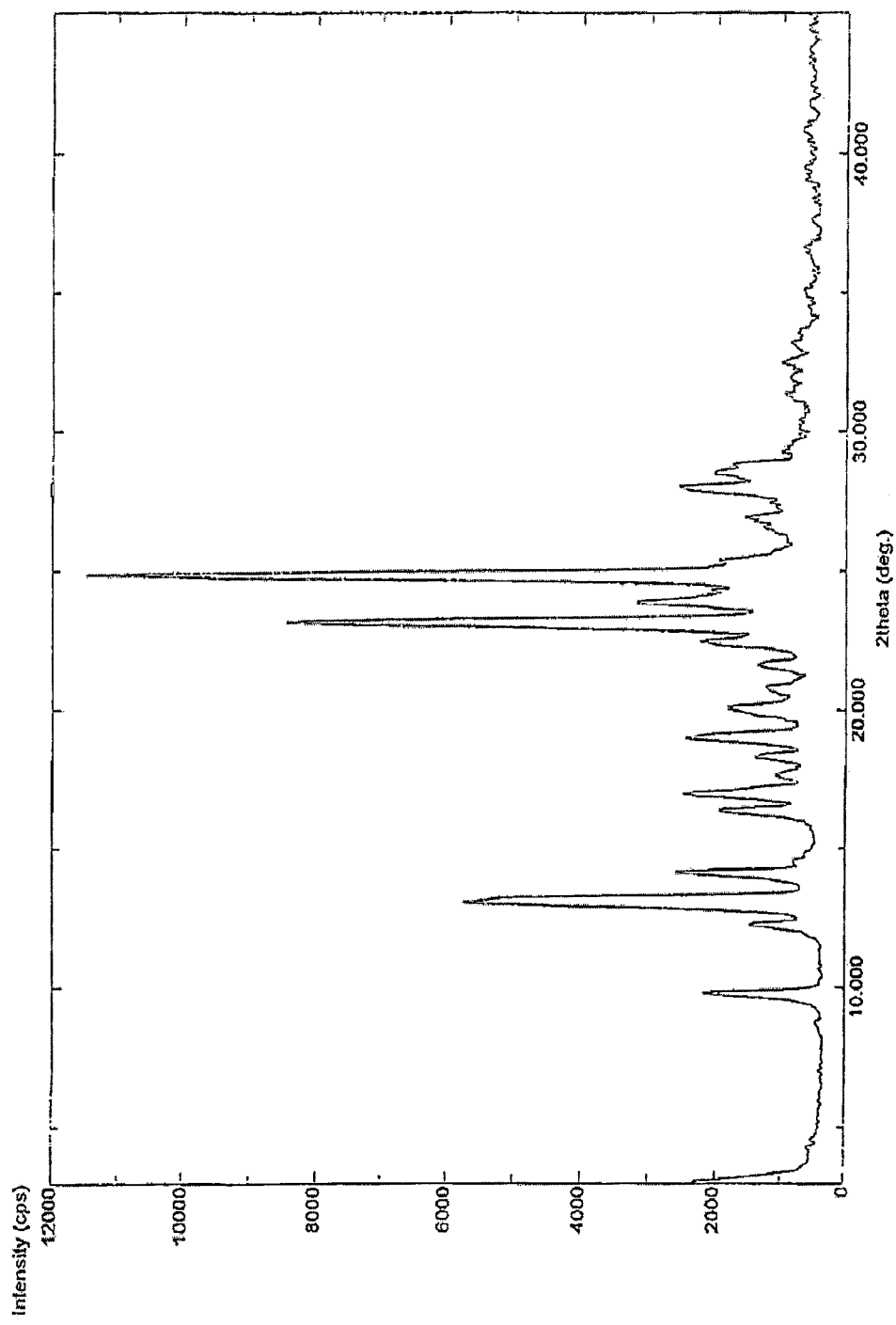
FIG. 11 shows the PXRD pattern of Sunitinib phosphate Form I

The XRPD is set forth in FIG. 11.

Example 14

Preparation of Sunitinib Phosphate Form II

Sunitinib (1.0 g) was suspended in methanol (152 mL), followed by addition of phosphoric acid (0.29 g) at 25-35° C. over a period of 15 minutes. After the stipulated time period, methanol was completely distilled off under vacuum below 45° C. The residue was treated with acetonitrile (38 mL) and refluxed. The reaction mass was maintained at reflux temperature for 60 minutes. The reaction mass was cooled to 25-35° C. for crystallization. The solid obtained was filtered, washed with acetonitrile, suck dried and dried under vacuum at 60° C. over 4-5 hr period to obtain sunitinib phosphate. (1.11 g; yield: 88%)

Purity by HPLC: 99.48%; phosphoric acid content: 19.37% (w/w)

TGA: 0.23-0.31%; DSC: onset peak 270° C. and endset at 273° C.

IR (in cm$^{-1}$): 3414, 2978, 1667, 1628, 1573, 1513, 1477, 1390, 1325, 1304, 1260, 1239, 1197, 1147, 1060, 945, 872, 846, 796, 665, 608, 588, 525.

Figure 12:
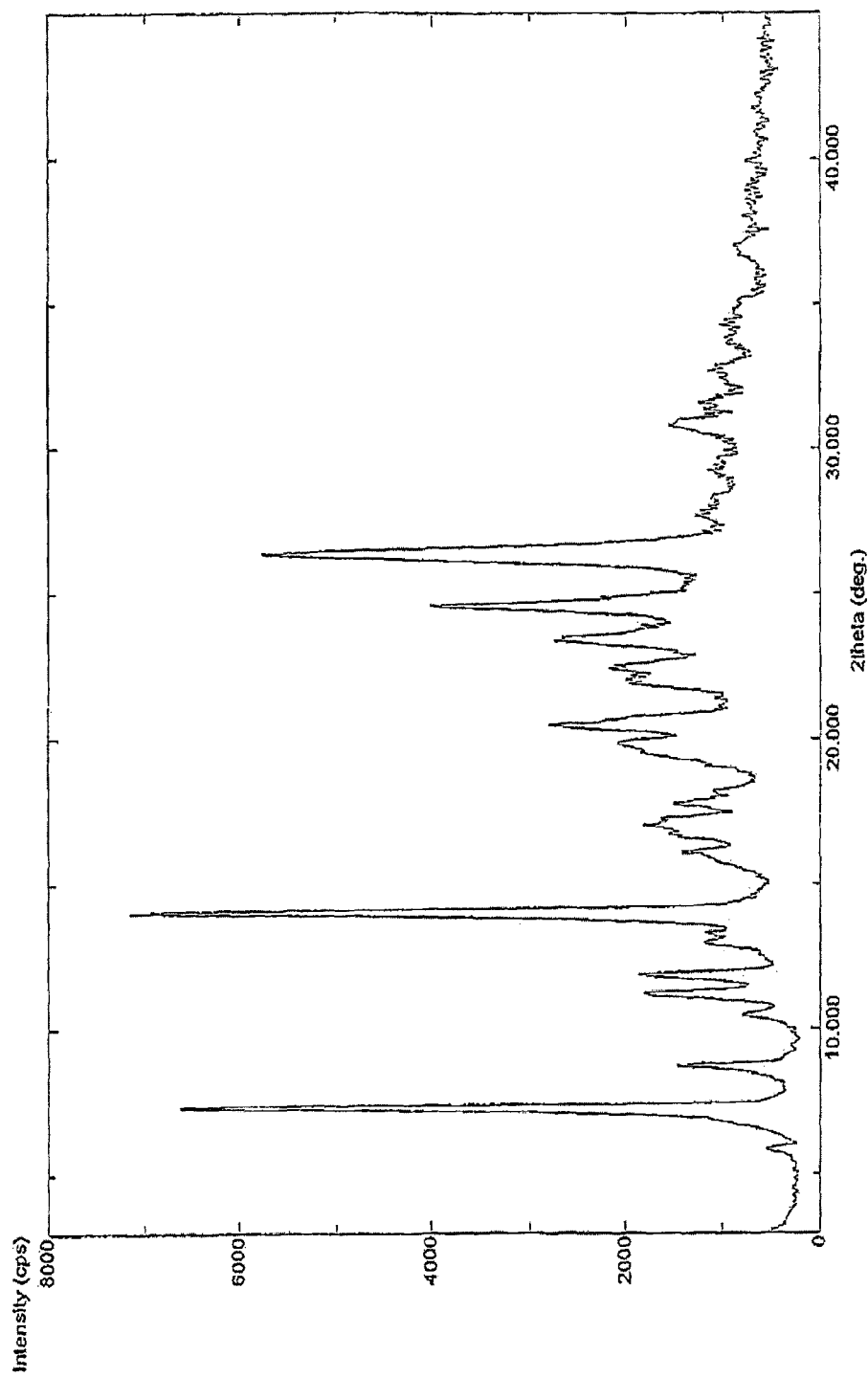
FIG. 12 shows the PXRD pattern of Sunitinib phosphate Form II

The XRPD is set forth in FIG. 12.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. A process for the preparation of sunitinib of Formula I or acid addition salts thereof,

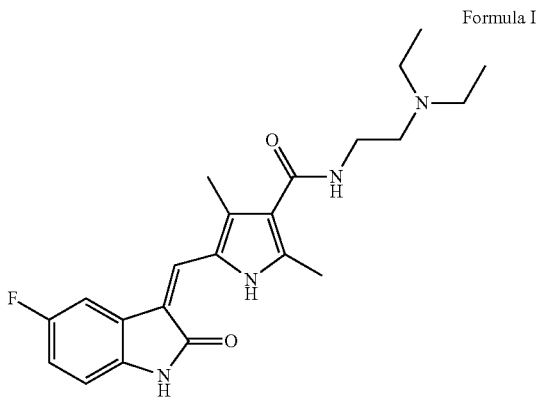 [SMILES: CCN(CC)CCNC(=O)c1c(C)[nH]c(/C=C2\C(=O)Nc3ccc(F)cc32)c1C]

Formula I the process comprising the steps of:
a) reacting 5-((Z)-(5-fluoro-2-oxoindolin-3-yliden) methyl)-2,4-dimethyl-1H-pyrrole-3-carboxylic acid of Formula II

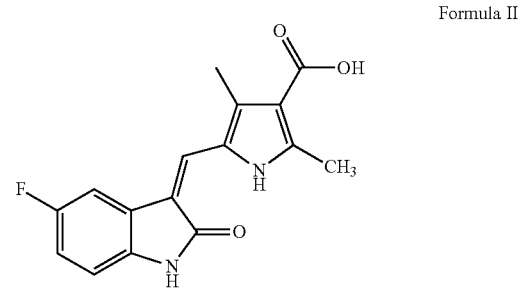 [SMILES: Cc1[nH]c(/C=C2\C(=O)Nc3ccc(F)cc32)c(C)c1C(=O)O]

Formula II with a sulfonylating agent to obtain an activated compound of Formula III,

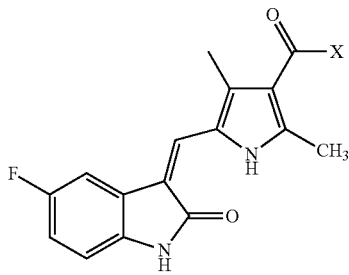

Formula III wherein X represents a sulfonyl; and
  b) amidating the compound of Formula III with N,N-diethyl ethylene diamine in an organic solvent to obtain sunitinib.

2. The process of claim 1, wherein the sulfonyl group is an alkyl sulfonyl or aryl sulfonyl, wherein alkyl represents $C_{1-4}$ linear or branched chain alkyl and aryl represents alkyl substituted or unsubstituted phenyl group.

3. The process of claim 1, wherein the sulfonylating agent is p-toluene sulfonyl chloride and the sulfonyl is p-toluene sulfonyl.

4. The process of claim 1, wherein step a) is carried out in presence of a base and a catalyst in an organic solvent.

5. The process of claim 4, wherein the base is selected from the group consisting of triethylamine, tributylamine, diisopropylethylamine, diethylamine, N-methylmorpholine, pyridine, N,N-dimethylaniline, N,N-diethylaniline, and mixtures thereof.

6. The process of claim 4, wherein the organic solvent is selected from the group consisting of formamide, dimethylformamide, dimethylacetamide, hexamethylphosphoric triamide, and mixtures thereof.

7. The process of claim 4, wherein the catalyst is N,N-dimethyl amino pyridine.

8. The process of claim 1, wherein the organic solvent of step b) is selected from the group consisting of formamide, dimethylformamide, dimethylacetamide, hexamethylphosphoric triamide, and mixtures thereof.

9. The process of claim 1, wherein step a) is carried out in presence of pyridine, N,N-dimethyl amino pyridine, and dimethylformamide.

10. The process of claim 1, further comprising the step of c) treating the sunitinib base with malic acid to obtain sunitinib malate salt.

11. A compound of formula III

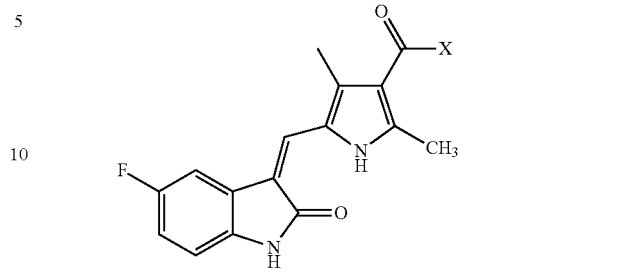

Formula III wherein X represents a sulfonyl.

12. The compound of claim 11, wherein X is p-toluene sulfonyl.

13. A process for the preparation of compound of formula III

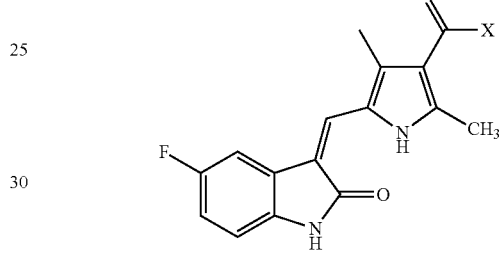

wherein X represents a sulfonyl,
  or a pharmaceutically acceptable salt thereof, the process comprising the step of reacting 5-((Z)-(5-fluoro-2-oxoindolin-3-ylidene) methyl)-2,4-dimethyl-1H-pyrrole-3-carboxylic acid of Formula II

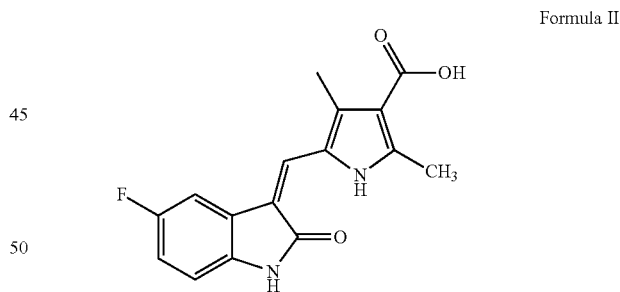

Formula II with a sulfonylating agent in presence of a base and a catalyst in an organic solvent to form a compound of Formula III.

* * * * *